(12) United States Patent
Park et al.

(10) Patent No.: US 9,173,637 B2
(45) Date of Patent: Nov. 3, 2015

(54) MINIATURE FORWARD-LOOKING ULTRASOUND IMAGING MECHANISM ENABLED BY LOCAL SHAPE MEMORY ALLOY ACTUATOR

(71) Applicant: Volcano Corporation, San Diego, CA (US)

(72) Inventors: Byong-Ho Park, Cincinnati, OH (US); Oren Levy, Emerald Hills, CA (US)

(73) Assignee: Volcano Corporation, San Diego, CA (US)

( * ) Notice: Subject to any disclaimer, the term of this patent is extended or adjusted under 35 U.S.C. 154(b) by 360 days.

(21) Appl. No.: 13/888,023

(22) Filed: May 6, 2013

(65) Prior Publication Data

US 2013/0269174 A1    Oct. 17, 2013

Related U.S. Application Data

(63) Continuation of application No. 12/992,814, filed as application No. PCT/US2009/044218 on May 15, 2009, now Pat. No. 8,454,519.

(60) Provisional application No. 61/077,111, filed on Jun. 30, 2008, provisional application No. 61/054,063, filed on May 16, 2008.

(51) Int. Cl.
| | |
|---|---|
| *A61B 8/00* | (2006.01) |
| *A61B 8/12* | (2006.01) |
| *A61B 5/00* | (2006.01) |

(52) U.S. Cl.
CPC ............. *A61B 8/4466* (2013.01); *A61B 5/445* (2013.01); *A61B 8/4461* (2013.01); *A61B 8/4494* (2013.01); *A61B 5/0066* (2013.01); *A61B 5/0084* (2013.01); *A61B 8/12* (2013.01); *A61B 8/4444* (2013.01); *Y10T 29/49005* (2015.01)

(58) Field of Classification Search
None
See application file for complete search history.

(56) References Cited

U.S. PATENT DOCUMENTS

| 4,841,977 A | 6/1989 | Griffith et al. |
| 5,379,772 A | 1/1995 | Imran |
| 2002/0107447 A1 | 8/2002 | Suorsa et al. |

(Continued)

FOREIGN PATENT DOCUMENTS

| JP | 05-285140 A | 11/1993 |
| JP | 09-505490 A | 6/1997 |
| WO | WO 95/07658 A1 | 3/1995 |

OTHER PUBLICATIONS

International Searching Authority/Korean Intellectual Patent Office, "Notification of Transmittal of the International Search Report and the Written Opinion of the International Searching Authority, or the Declaration," for PCT/US2009/044218, mailed Dec. 29, 2009, 11 pages.

(Continued)

*Primary Examiner* — Katherine Fernandez
*Assistant Examiner* — Michael Kellogg
(74) *Attorney, Agent, or Firm* — Haynes and Boone, LLP

(57) ABSTRACT

The present invention relates to a new forward-looking ultrasound device including a local actuator embedded inside an elongate member such as a guide wire or catheter. The present invention includes an ultrasound transducer element configured to engage with the local actuator and rotate about an axis of rotation at least when the ultrasound transducer element and the local actuator are engaged. Also disclosed are methods of using the same.

20 Claims, 13 Drawing Sheets

(56) References Cited

U.S. PATENT DOCUMENTS

| | | |
|---|---|---|
| 2003/0229286 A1 | 12/2003 | Lenker |
| 2006/0173348 A1 | 8/2006 | Wilser et al. |
| 2007/0016062 A1 | 1/2007 | Park et al. |
| 2007/0016063 A1 | 1/2007 | Park et al. |
| 2008/0081947 A1 | 4/2008 | Irion et al. |
| 2009/0264768 A1 | 10/2009 | Courtney et al. |

OTHER PUBLICATIONS

Japanese Office Action and English Translation received in Japanese Application No. 2011-509772, dated Nov. 12, 2013, 4 pages.

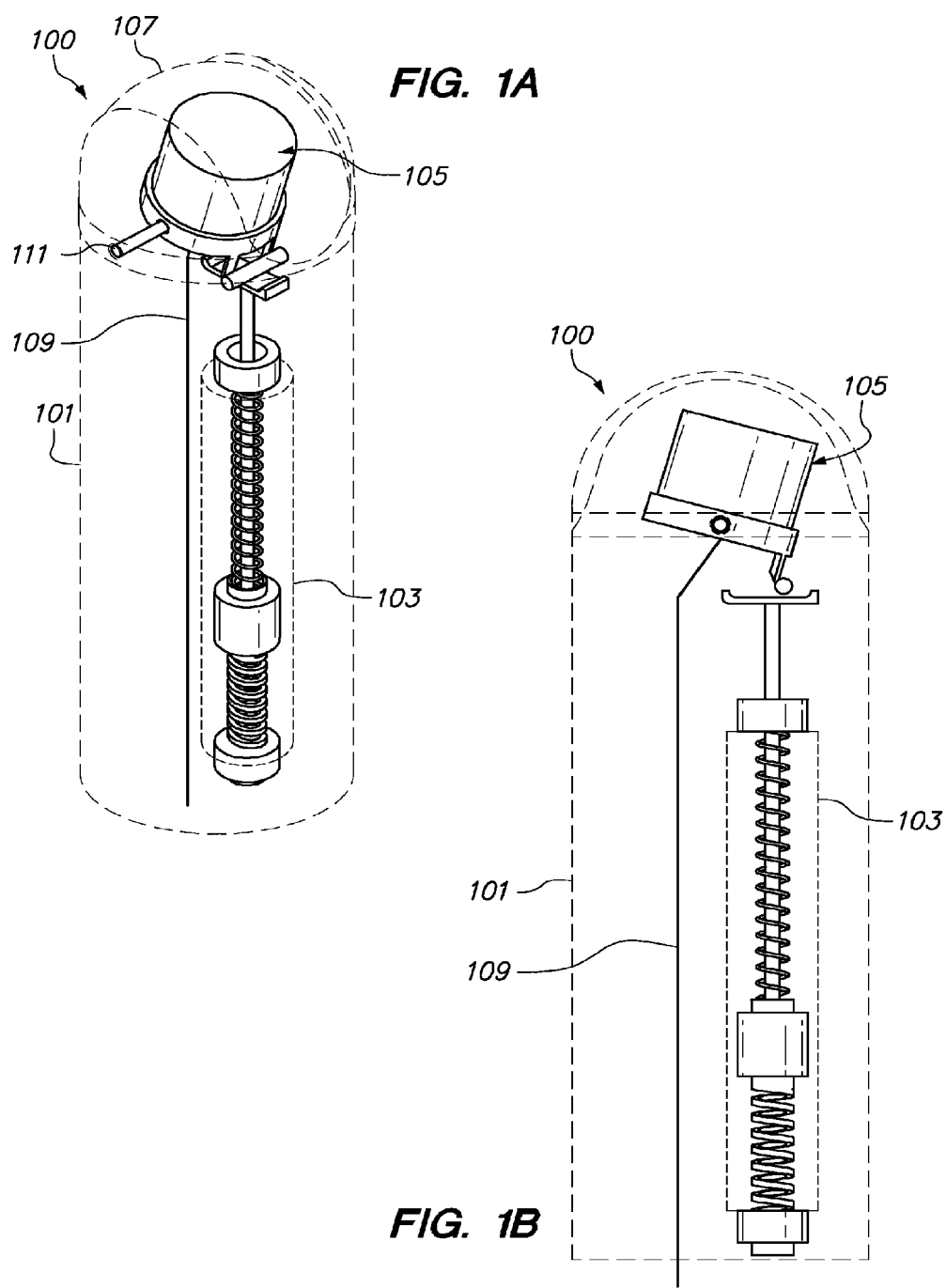

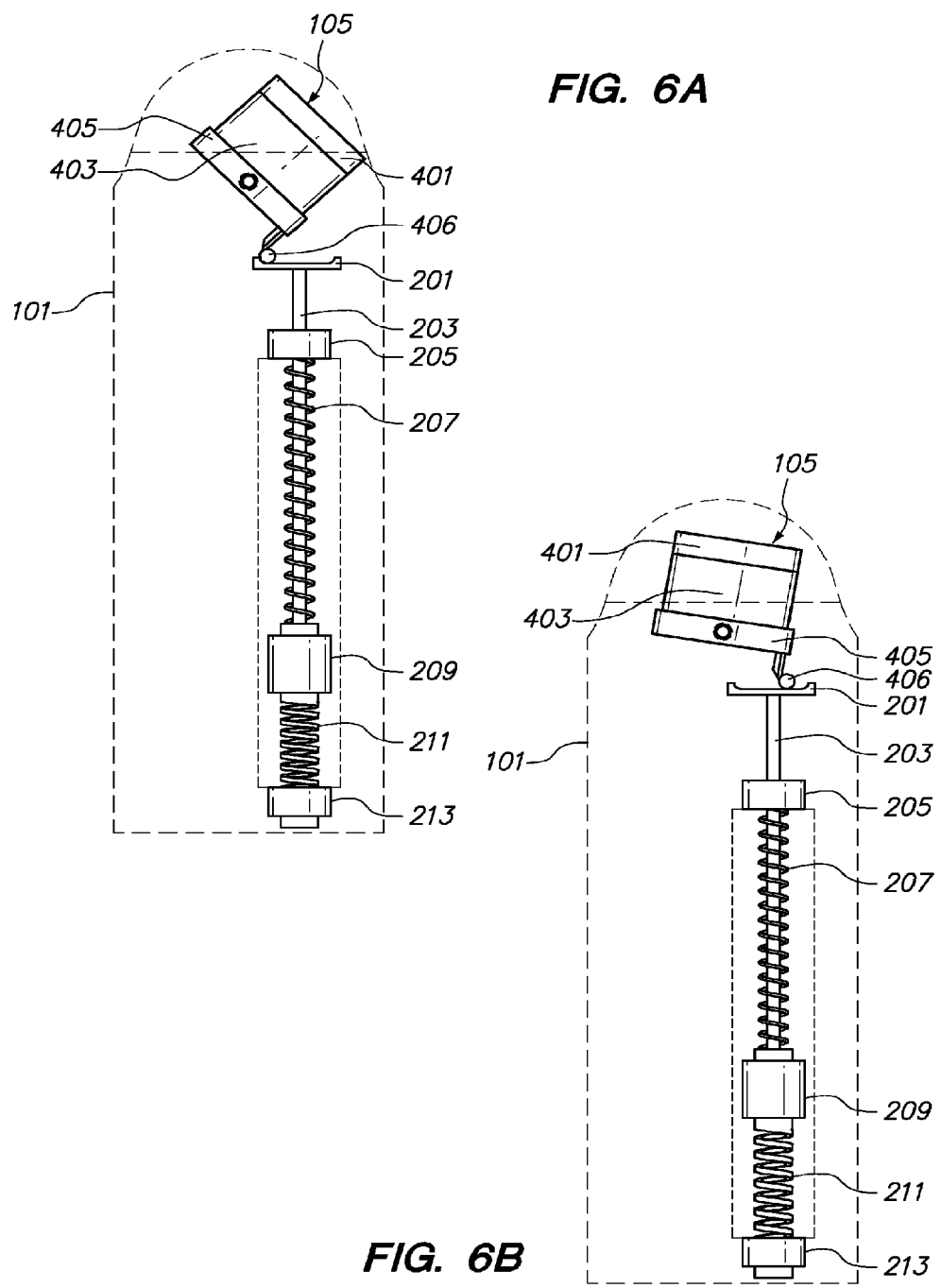

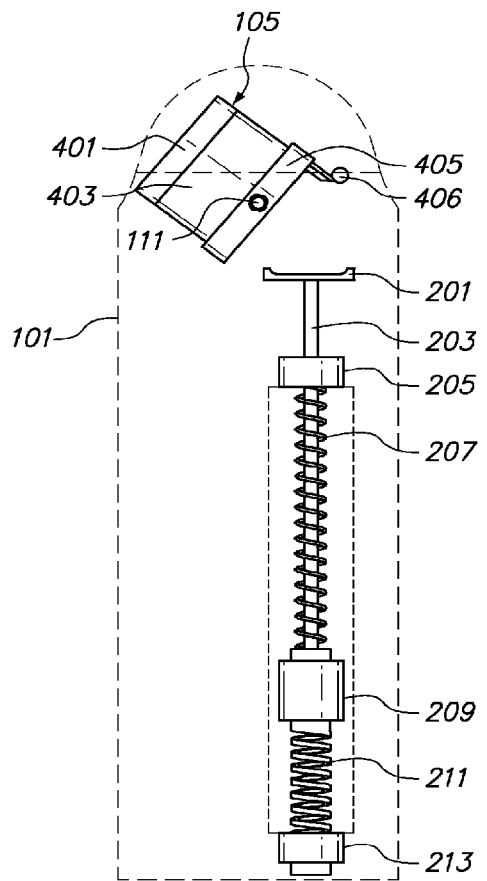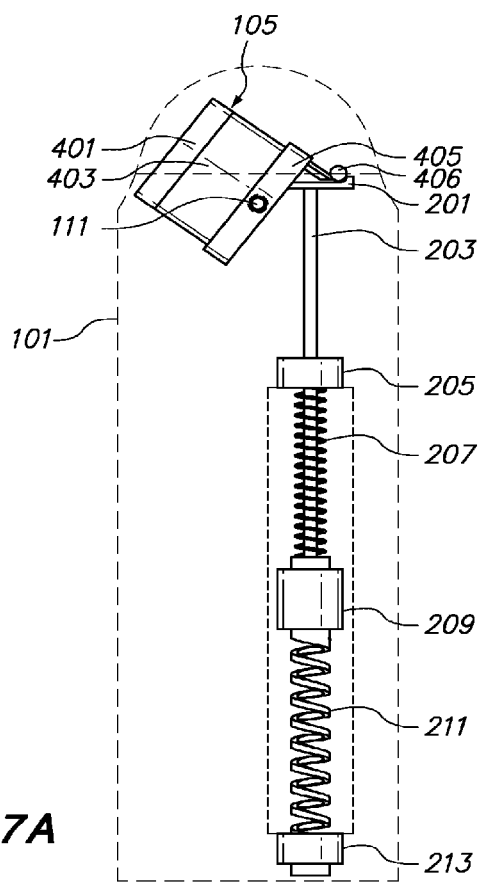

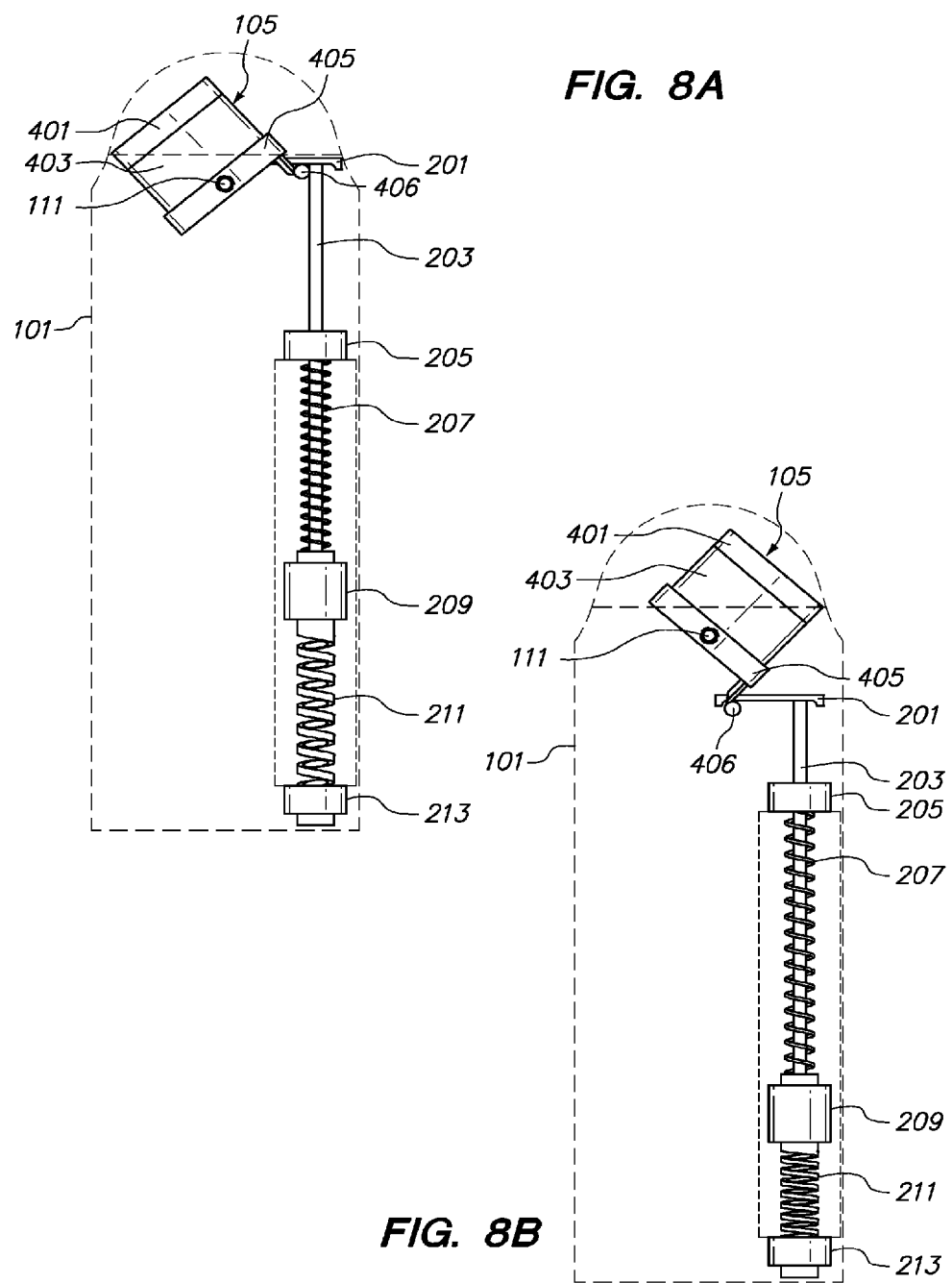

MINIATURE FORWARD-LOOKING ULTRASOUND IMAGING MECHANISM ENABLED BY LOCAL SHAPE MEMORY ALLOY ACTUATOR

CROSS-REFERENCE TO RELATED APPLICATIONS

This application is a continuation of U.S. patent application Ser. No. 12/992,814 filed on Mar. 7, 2011, which claims priority to Patent Cooperation Treaty Application Number PCT/US2009/044218 filed on May 15, 2009, which claims the benefit of U.S. Provisional Application No. 61/054,063 filed on May 16, 2008, titled "MINIATURE FORWARD-LOOKING ULTRASOUND IMAGING MECHANISM ENABLED BY LOCAL SHAPE MEMORY ALLOY ACTUATOR," and U.S. Provisional Application. No. 61/077,111 filed on Jun. 30, 2008, titled "MINIATURE FORWARD-LOOKING ULTRASOUND IMAGING MECHANISM ENABLED BY LOCAL SHAPE MEMORY ALLOY ACTUATOR," all of which are hereby expressly incorporated by reference in their entireties.

BACKGROUND

Embodiments disclosed herein concern a miniature actuator which is useful in intravascular imaging devices including intravascular ultrasound (IVUS), and optical coherence tomography (OCT). The miniature actuator mechanism and ultrasound or OCT imaging device is preferably embedded in an elongated body such as an intravascular guide wire or catheter to provide imaging guidance in various interventional applications.

DESCRIPTION OF THE RELATED ART

Coronary artery disease is very serious and often requires an emergency operation to save lives. The main cause of coronary artery disease is the accumulation of plaque inside a person's vasculature, which eventually occludes blood vessels. Several solutions are available, for example, balloon angioplasty, rotational atherectomy, and intravascular stents, to open up the clogged section, which is called stenosis. Traditionally, during the operation, surgeons rely on X-ray fluoroscopic images that are basically planary images showing the external shape of the silhouette of the lumen of blood vessels. Unfortunately, with X-ray fluoroscopic images, there is a great deal of uncertainty about the exact extent and orientation of the atherosclerotic lesions responsible for the occlusion, making it difficult to find the exact location of the stenosis. In addition, though it is known that restenosis can occur at the same place, it is difficult to check the condition inside the vessels after surgery. Intravascular imaging would be valuable during interventional procedures to facilitate navigation and for intraoperative feedback. For example, the precise placement and appropriate expansion of stents would benefit from simultaneous intravascular imaging. Existing intravascular imaging devices are too large and are not flexible enough to be placed simultaneously with other devices.

In order to resolve these issues, an ultrasonic transducer device has been utilized for endovascular intervention to visualize the inside of the blood vessels. To date, the current technology is mostly based on one or more stationary ultrasound transducers or rotating a single transducer in parallel to the blood vessels by means of a rotating shaft which extends through the length of the catheter to a motor or other rotary device located outside the patient. These devices have limitations in incorporating other interventional devices into a combination device for therapeutic aspects. They require a large space inside catheter such that there is not enough room to accommodate other interventional devices. Also, due to the nature of the rotating shaft, the distal end of the catheter is very stiff and it is hard to navigate through tortuous arteries. The high speed rotating shaft also contributes to distorted nonuniform images when imaging a tortuous path in the vasculature. OCT has also been utilized to visualize the intravascular space based on differential reflectance, but most existing OCT devices rely on a rotating fiber optic which extends along the length of the device. This approach also has problems, for example, the manipulation, spinning and scanning motion required with respect to a delicate glass or polycarbonate optical fiber; the actuator mechanism located outside the patient and tip located inside the patient are significantly distant from one another, leading to inefficiencies and control issues arising from the torque created by a long, spinning member; and remote mechanical manipulation and a long spinning element distort the image due to nonuniform rotational distortion.

Additionally, current devices are mainly side-looking devices that are not able to provide valuable information to be used as guidance during invasive procedures. Forward-looking ultrasound imaging is essential in guiding an interventional device for treatment in a timely manner. For example, when implanting a heart pacemaker, electrical leads need to be implanted in precise locations. Currently there is no accurate forward-looking imaging device to direct the leads to the right locations. Thus, physicians are required to blindly rely on guide catheters and spend more time than needed when performing procedures. Also, patients are being over exposed to unnecessary radiation and toxic contrast agents involved with fluoroscopy. Given the numerous difficulties with current intravascular imaging devices, there is a need for an improved forward-looking intravascular imaging device.

SUMMARY

One embodiment of the invention is a forward-looking intravascular ultrasound device that includes an ultrasound transducer that rotates around an axis of rotation and a local actuator configured to cause the ultrasound transducer to rotate. The linear actuator includes a movable element that moves back and forth from a first position to a second position. The movable element is connected to at least one SMA actuator that is expands or contracts when activated in order to move the movable element from the first position to the second position or from the second position to the first position. The movable element engages the ultrasound transducer and causes it to rotate around the axis of rotation to create a forward-looking sweeping motion. The ultrasound transducer may continue to rotate even after it disengages from the movable element due to the moment of inertia of the transducer or some other amplifying force, for example, a biasing force.

One embodiment of the invention is a forward-looking intravascular ultrasound device comprising an elongated body having a longitudinal end, an interior surface, an exterior surface, a proximal end, and a distal end; an ultrasound transducer element disposed at least partially in the distal end of the elongated body and configured to rotate between at least a primary position and a secondary position about an axis of rotation that is generally normal to the longitudinal axis; and a local actuator comprising a first element, wherein the first element is secured to and does not move relative to the body; a movable element, wherein the movable element is configured to move longitudinally substantially parallel to the longitudinal axis between at least a first position and a second position, wherein the movable element is configured to engage the ultrasound transducer element at least when the movable element moves from the first position to the second position; a first SMA actuator coupled to the first element and the movable element, wherein the first SMA actuator is configured to switch between an activated and deactivated state, wherein the movable element moves from the first position to the second position upon activation of the first SMA actuator; and wherein the ultrasound transducer element rotates about the axis of rotation at least when the movable element and the ultrasound transducer element are engaged and the movable element moves from the first position to the second position. In another embodiment, the device comprises a biasing element coupled to the movable element and the first element, wherein the biasing element is configured to move the movable element from the second position to the first position. In yet another embodiment, the biasing element comprises a spring.

In another embodiment, the device described herein comprises a second element, wherein the second element is secured to and does not move relative to the body; and a biasing element coupled to the second element and the movable element, wherein the biasing element is configured to move the movable element from the second position to the first position. In some embodiments, the first and second elements are disposed along an axis that is substantially parallel to the longitudinal axis. In other embodiments, the first and second elements are disposed along an axis that is substantially normal to the longitudinal axis. In some embodiments, the biasing element comprises a spring. In other embodiments, the biasing element comprises a second SMA actuator, wherein the second SMA actuator has an activated and a deactivated state and when the second SMA actuator is activated it opposes motion of the movable element from the first position to the second position. In some embodiments, the cross-sectional shape of the distal end of the body is generally curvilinear and has a diameter of not more than about 0.200 inches.

Some embodiments of the device comprise an electrical wire connected to the ultrasound transducer element. In some embodiments, the device comprises a member coupled with the interior surface of the elongated body at or near the distal end, wherein the ultrasound transducer element is configured to rotate about the member between at least the primary position and the secondary position. In some embodiments, the electrical wire is coiled at least partially around the member. In some embodiments, the cam and ultrasound transducer element are not continuously engaged while the movable element moves from the second position to the first position.

In some embodiments, the angle of rotation the ultrasound transducer element rotates about the axis of rotation between the primary position and the secondary position is between about 5° and about 185°. In some embodiments, the angle of rotation the ultrasound transducer element rotates about the axis of rotation when the movable element moves from the first position to the second position is less than the angle of rotation the ultrasound transducer element rotates about the axis of rotation between the primary position and the secondary position. In some embodiments, the linear actuator is not fixed to the ultrasound transducer element. In some embodiments, the ultrasound transducer and cam are not engaged after the movable element reaches the second position and the ultrasound transducer continues to rotate about the axis of rotation towards the secondary position. In some embodiments, the ultrasound transducer element comprises a biasing element configured to bias the ultrasound transducer towards the secondary position. In some embodiments, the biasing element comprises a spring. In some embodiments, the biasing element comprises an electrical wire. In some embodiments, the ultrasound transducer element comprises a high density material and a transducer crystal. In some embodiments, the volume of the ultrasound transducer element is at least about 0.1 cubic mm. In some embodiments, the mass of the ultrasound transducer element is at least about 1 mg. In some embodiments, the ultrasound transducer element is configured to transmit ultrasound energy at an angle of between about 15° and 165° relative to an axis that is generally normal to the longitudinal axis and the axis of rotation. In some embodiments, the elongated body comprises a guide wire. In some embodiments, the first element comprises an aperture, and the movable element is disposed at least partly within the aperture. In some embodiments, the movable element comprises a shaft and in some embodiments, the movable element comprises a shaft connected to a cam.

Another embodiment is a method of visualizing the interior of a patient's vascular, the method comprising inserting the distal end of the distal end of a device disclosed herein into the vasculature of the patient; generating an ultrasound signal from the ultrasound transducer element; activating the first SMA actuator such that the movable element moves from the first position to the second position and the cam engages the ultrasound transducer element; deactivating the first SMA actuator such that the biasing element moves the movable element from the second position to the first position; receiving an ultrasound signal reflected from the interior of the vasculature on the ultrasound transducer element; and producing an image from the reflected signal.

Also disclosed herein is a forward-looking intravascular ultrasound device comprising an elongated body having a longitudinal axis, an exterior surface, a proximal end, and a distal end; an ultrasound transducer means disposed in the distal end of the elongated body and configured to rotate about an axis of rotation that is generally normal to the longitudinal axis; and a local actuator means configured to engage the ultrasound transducer means and cause the ultrasound transducer means to rotate about the axis of rotation at least when the local actuator means and ultrasound transducer means are engaged.

BRIEF DESCRIPTION OF THE DRAWINGS

FIG. 1A is a partial cut-away perspective view showing an embodiment of a forward-looking ultrasound imaging device.

FIG. 1B is a partial cut-away side view of the forward-looking ultrasound imaging device depicted in FIG. 1A.

FIG. 6A is a partial cut-away side view of an embodiment of a forward-looking ultrasound imaging device.

FIG. 6B is a partial cut-away side view of the forward-looking ultrasound imaging device shown in FIG. 6A showing the ultrasound transducer element in a different position.

FIG. 6C is a partial cut-away side view of the forward-looking ultrasound imaging device shown in FIG. 6B showing the ultrasound transducer element in a different position.

FIG. 7A is a partial cut-away side view of an embodiment of a forward-looking ultrasound imaging device.

FIG. 8A is a partial cut-away side view of an embodiment of a forward-looking ultrasound imaging device.

FIG. 8B is a partial cut-away side view of the forward-looking ultrasound imaging device shown in FIG. 8A showing the ultrasound transducer element in a different position.

DETAILED DESCRIPTION

Figure 2A:
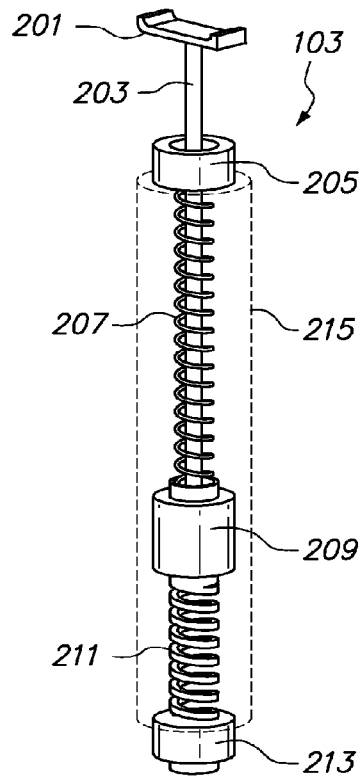
FIG. 2A is a partial cut-away perspective view showing an embodiment of a local actuator including a movable element.

Embodiments disclosed herein relate to imaging devices for intravascular imaging, although the present invention is not limited to this preferred application. Imaging of the intravascular space, particularly the interior walls of the vasculature can be accomplished by a number of different means. Two of the most common are the use of ultrasound energy, commonly known as intravascular ultrasound (IVUS) and optical coherence tomography (OCT). Both of these methods are optimized when the instruments (IVUS or OCT) used for imaging a particular portion of the vasculature are repeatedly swept over the area being image, for example, with a back and forth sweeping motion or rotational sweeping motion.

To address the limitations in current devices, a new intravascular imaging device is described based on a Shape Memory Alloy (SMA) actuator device embedded inside an elongated body such as a guide wire or catheter. Embodiments of the present invention utilizes a novel SMA device to provide forward-looking imaging by providing movement for an ultrasound transducer or OCT element. Since this novel SMA actuator device can be easily fabricated in micro-scale using laser machining or other fabrication techniques, it provides an advantage over existing imaging devices because it offers the ability to miniaturize the overall size of the device, while the use of multiple transducer crystals maximizes field of view. The small dimensions of the actuator device of the invention allow for the cross-sectional area of the elongated body in which it is housed to be very small. The outside width of the elongated body, such as a guide wire or catheter containing an imaging device described herein can be as small as from about 0.0050" to about 0.200". The outside width for elongated bodies can be larger when the imaging device is combined with other interventional devices, although the outside width of these devices can be as small as 0.060" or smaller. Current catheters containing IVUS range from 0.70 mm to 3 mm in outside diameter.

Additionally, embodiments of the present invention address limitations stemming from fatigue failure due to the range of displacement in SMA actuator devices. Ultrasound devices must be able to operate for a certain period of time when used in invasive procedures. However, the life of the SMA actuator may be limited by fatigue failure after a certain amount of cycles of scanning. Fatigue failure can be delayed if the range of displacement the SMA actuator undergoes is limited. On the other hand, a large scanning motion is required to produce quality images during an invasive procedure. Embodiments disclosed herein balance these two concerns and incorporate an SMA actuator that undergoes a small displacement and applies an impulse force on the transducer. The transducer continues to rotate after the SMA actuator applies the impulse force due to the moment of inertia of the transducer and/or another biasing force, for example, a spring. Thus, embodiments disclosed herein can produce a large scanning motion while limiting the displacement of the SMA actuator and preventing or delaying fatigue failure of the SMA actuator.

Existing single-element ultrasound (IVUS) devices are based on a rotating shaft with a driving motor located externally. An imaging tip with a transducer or mirror is mounted directly on the rotating shaft. As a result, when the rotating shaft has a slight change in its motion, it induces a non-uniform rotational distortion (NURD) in the actual image. NURD may happen when there is a kink along the length of the rotating shaft. Since shafts in current IVUS devices are relatively big, they tend to kink when going through a tortuous path, for example, a vasculature, resulting in a NURD problem in imaging. NURD happens in some instances because there is no way of knowing where the imaging tip is pointing if the device is not forward-looking. NURD can be reduced or eliminated if there is a feedback signal available from the distal end as provided in some embodiments disclosed herein.

Embodiments disclosed in this application do not require a rotating shaft or fiber optic along the length of the catheter, allowing for a more flexible catheter or guide wire, and providing room for other interventional devices. In addition, the lack of a rotating shaft eliminates the problems mentioned above with current OCT technology, for example, NURD. Another advantage of some of the embodiments disclosed herein is the elimination of non-uniform distortion of the acquired image that occurs in current IVUS devices. In one embodiment, the imaging mechanism (e.g., ultrasound transducer element) is located at the distal end of the device and does not continuously rotate but oscillates back and forth in a rotational sweeping motion. Additionally, an optional miniature spring can be embedded in the imaging mechanism and work as a position sensor or strain gauge to provide a feedback signal to the imaging system.

As used herein, "elongated body" includes any thin, long, flexible structure which can be inserted into the vasculature of a patient. Elongated bodies include, for example, intravascular catheters and guide wires. The local actuator is disposed in the distal end of the elongated body. As used herein, "distal end" of the elongated body includes the portion of the elongated body that is first inserted into the patient and is typically the most distant from the point of insertion after the elongated body enters the patient. As elongated bodies can be solid, some will include a housing portion at the distal end for receiving the local actuator. Such housing portions can be tubular structures attached to the side of the distal end or attached to the distal end of the elongated body. Other elongated bodies are tubular and have one or more lumens in which the actuator mechanism can be housed at the distal end.

"Connected" and variations thereof as used herein include direct connections, such as being glued or otherwise fastened directly to, on, within, etc. another element, as well as indirect connections where one or more elements are disposed between the connected elements.

"Secured" and variations thereof as used includes methods by which an element is directly secured to another element, such as being glued or otherwise fastened directly to, on, within, etc. another element, as well as indirect means of securing two elements together where one or more elements are disposed between the secured elements.

Movements which are "counter" are movements in the opposite direction. For example, if the ultrasound transducer element is rotated clockwise, rotation in a counterclockwise direction is a movement which is counter to the clockwise rotation. Similarly, if the movable element is moved substantially parallel to the longitudinal axis of the elongate member in a distal direction, movement substantially parallel to the longitudinal axis in a proximal direction is a counter movement.

As used herein, "light" or "light energy" encompasses electromagnetic radiation in the wavelength range including infrared, visible, ultraviolet, and X rays. The preferred range of wavelengths for OCT is from about 400 nm to about 1400 nm. For intravascular applications, the preferred wavelength is about 1200 to about 1400 nm. Optical fibers include fibers of any material which can be used to transmit light energy from one end of the fiber to the other.

Embodiments of the invention will now be described with reference to the accompanying Figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention can include several novel features, no single one of which is solely responsible for its desirable attributes or which is essential to practicing the inventions herein described.

FIGS. 1A and 1B illustrate an embodiment of a novel forward-looking intravascular ultrasound device 100 capable of sweeping or scanning forward of the distal end of the device 100 to produce IVUS or OCT images. As shown in FIG. 1A, the device 100 may include an elongated body 101 having a distal end, a proximal end, and a longitudinal axis. The elongated body 101 is any size. In one embodiment, the elongated body 101 is small enough to fit inside a standard guide catheter with an inner diameter that is, is about, is not less than, is not less than about, is not more than, or is not more than about 12Fr, HFr, 10Fr, 9Fr, 8Fr, 7Fr, 6Fr, 5Fr, 4Fr, 3Fr, 2Fr, 1Fr, or falls within a range defined by, and including, any two of these values. Thus, the outside diameter of the elongated body 101 is preferably less than the inner diameter of the standard guide catheter in some embodiments.

The elongated body 101 has at least a portion 107 which is at least partially sonolucent (e.g., permits the passage of at least some ultrasound waves without absorbing or reflecting them back to their source). The portion 107 can be a window made of an ultrasound transparent material, a material which is partially or substantially transparent to ultrasound energy, or the portion 107 can be a window, opening, or aperture. In some embodiments, the entire elongated body 101 or the majority of the distal end of the elongated body 101 is formed of a substantially sonolucent material.

In some embodiments, portions of the elongate member 101 are solid and other portions, for example, the distal end, include housing portions capable of receiving other objects. Such housing portions can be tubular structures attached to the side of the distal end or attached to the distal end of the elongated body 101. Other elongated bodies 101 are tubular and have one or more lumens capable of housing other objects in the distal end. The elongated body 101 shown in FIGS. 1A and 1B houses an ultrasound transducer element 105, a local actuator 103, a coupling member 111, and an electrical wire 109. In some embodiments, the electrical wire 109 is connected to the ultrasound transducer element 105 and wrapped at least partially around the coupling member 111. In some embodiments, the transducer element 105 comprises, or is secured directly or indirectly to the coupling member 111.

The local actuator 103 is configured to engage (e.g., contact, push, or pull) the ultrasound transducer element 105 and cause the ultrasound transducer element 105 to rotate in a first direction and/or a second direction counter to the first direction about an axis of rotation. In some embodiments, the axis of rotation is generally normal to the longitudinal axis. In some embodiments, the ultrasound transducer element 105 is directly connected or coupled with the elongated body 101 and configured to rotate relative to the elongated body 101 about an axis of rotation. In some embodiments, the axis of rotation is substantially parallel to the coupling member 111. In other embodiments, the ultrasound transducer element 105 is coupled with a member 111 that extends from an interior surface of the elongated member 101 such that the ultrasound transducer element 105 rotates about the member 111.

Figure 2B:
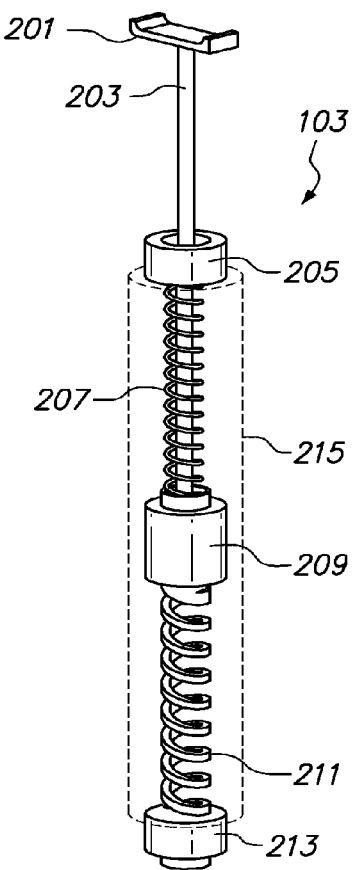
FIG. 2B is a partial cut-away perspective view showing the local actuator depicted in FIG. 2A with the movable element in a different position than shown in FIG. 2A.

FIGS. 2A and 2B show an embodiment of a local actuator 103 that includes a first element 205 and a second element 213 which are secured relative to the interior of the elongated body 101 to anchor or hold the device 103 in place relative to the elongated body 101 such that the first element 205 and second element 213 do move relative to the elongated body 101. In some embodiments, the first and second elements 205, 213 are disposed anywhere within the elongated body 101, for example, at or near the distal end.

In some embodiments, the local actuator 103 includes a movable element 209 that is configured to move relative to the first element 205, the second element 213, and the elongated body 101. In some embodiments, the movable element 209, the first element 205, and the second element 213 are disposed along an axis within the elongated body 101, for example, an axis that is substantially parallel to the longitudinal axis. In one embodiment, the movable element 209, the first element 205, and the second element 213 are disposed along an axis that is substantially normal to the longitudinal axis or an axis that is substantially not parallel to the longitudinal axis. In some embodiments, the movable element 209 is disposed between the first element 205 and the second element 213 and configured to move between the first element 205 and the second element 213. In one embodiment, the movable element 209 moves in a first direction along an axis that is substantially parallel to the longitudinal axis and in a second direction that is counter to the first direction. In another embodiment, the movable element 209 is configured to move in more than one range of motion, for example, along an axis that is substantially parallel to the longitudinal axis as well as rotationally about the longitudinal axis.

In one embodiment, the first element 205 is connected or coupled with the movable element 209 by a first shape memory alloy (SMA) actuator 207 which moves the movable element 209 when activated as described in more detail below with reference to FIGS. 3A and 3B. The first SMA actuator 207 can be fabricated from any known material with shape memory characteristics, for example, nitinol. As known by those of skill in the art, SMAs can be fabricated to take on a predetermined shape when activated. In some embodiments, SMAs can be fabricated to expand or contract when activated from their deactivated state. In other embodiments, SMAs can be configured to expand or contact and rotate when activated from their deactivated state. Activation of a SMA actuator consists of heating the SMA such that it adopts its trained shape. In some embodiments, activation is accomplished by applying an electric current across the SMA element. Deactivation of a SMA actuator can be accomplished by turning off current to the SMA or otherwise cooling the SMA in order to allow the SMA to return to its pliable state as it cools. In some embodiments, there are electrical contacts and an insulated area in the local actuator 103 which allow activation of the first SMA actuator 207. Activation of the first SMA actuator 207 to its trained shape results in a force which can be utilized by the local actuator 103 to move the movable element 209 in a first direction, for example, along an axis between the first element 205 and the second element 213.

As one of skill in the art will recognize, SMA actuators can take numerous shapes and configurations other than the helical shape of the first SMA actuator 207 shown in FIG. 1. For example, a SMA is a straight wire, circular wire, or spiral wire. A SMA does not need to have a circular cross-section, for example, it can have a square, rectangular, polygonal, generally curvilinear, or irregularly shaped cross-section. In some embodiments, multiple SMA elements are coupled together to form a single SMA actuator 207. Additionally, other types of actuators, for example, an electro-magnetic motor, a solenoid, or piezoelectric actuator, can be used in place of a first SMA actuator 207 in the local actuator 103. By alternatively activating and deactivating the first SMA actuator 207, a cyclical movement of the moveable element 209 will result. This cyclical movement can be rotational about the longitudinal axis or back and forth along an axis that is generally and/or substantially parallel to the longitudinal axis.

The first SMA actuator 207 can be very small such that it has a width between about 5 µm and about 1000 µm, with the preferred size being between about 5 µm and about 100 µm. The first SMA actuator 207 preferably has a diameter that is, is about, is at least, is at least about, is not more than, is not more than about 5, 10, 20, 30, 40, 50, 60, 70, 80, 90, 100, 200, 300, 400, 500, 600, 700, 800, 900, or 1000 µm, or within a range defined by, and including, any two of these values. The range of lengths preferred for the first SMA actuator 207 in its relaxed or deactivated state ranges from about 20 µm to about 10 mm, with the preferred length being from about 200 µm to about 10 mm. The first SMA actuator 207 preferably has an overall length that is, is about, is at least, is at least about, is not more than, is not more than about 20, 30, 40, 50, 60, 70, 80, 90, 100, 200, 300, 400, 500, 600, 700, 800, 900 µm, 1, 2, 3, 4, 5, 6, 7, 8, 9, 10, 11, 12, 13, 14, 15, 16, 17, 18, 19, or 20 mm, or within a range defined by, and including, any two of these values.

In some embodiments, the second element 213 is connected or coupled with the movable element 209 by a biasing element 211. The biasing element 211 can be made from materials which are not rigid, including elastic, superelastic, and non-elastic materials. In some embodiments, the biasing element 211 comprises a spring, for example, a tension spring or compression spring. In other embodiments, the biasing element 211 comprises a second SMA actuator configured to move between activated and deactivated states. The biasing element 211 can be formed from various materials, including elastic alloys, for example, Cu—Al—Ni, Cu—Al, Cu—Zn—Al, Ti—V, and Ti—Nb alloys.

The biasing element 211 can be very small such that it has a width between about 5 µm and about 1000 µm, with the preferred size being between about 5 µm and about 100 µm. The biasing element 211 preferably has a diameter or width that is, is about, is at least, is at least about, is not more than, is not more than about, 5, 10, 20, 30, 40, 50, 60, 70, 80, 90, 100, 200, 300, 400, 500, 600, 700, 800, 900, or 1000 µm, or within a range defined by, and including, any two of these values. The range of lengths preferred for the biasing element 211 in its relaxed or deactivated state ranges from about 20 µm to about 10 mm, with the preferred length being from about 200 µm to about 10 mm. The biasing element 211 preferably has an overall length that is, is about, is at least, is at least about, is not more than, is not more than about, 20, 30, 40, 50, 60, 70, 80, 90, 100, 200, 300, 400, 500, 600, 700, 800, 900 µm, 1, 2, 3, 4, 5, 6, 7, 8, 9, 10, 11, 12, 13, 14, 15, 16, 17, 18, 19, or 20 mm, or within a range defined by, and including, any two of these values.

The biasing element 211 is configured to apply a force to the movable element 209 that opposes the force applied by the first SMA actuator 207 on the movable element 209. This opposing force can move the movable element 209 in a direction counter to the direction the movable element 209 moves when the first SMA actuator is activated. The movement of the movable element 209 can be appreciated by comparing FIGS. 2A and 2B. In FIG. 2A, the movable element 209 is in a first position (e.g., closer to the second element 213 than the first element 205). In FIG. 2B, the movable element 209 is in a second position (e.g., closer to the first element 205 than the second element 213).

In an alternative embodiment, one or both of the first and second elements 205, 213 are eliminated and one end of the first SMA actuator 207 and/or the biasing element 211 are secured directly to the elongated body 101 or housing 215. In another alternative embodiment, one or both of the first and second elements 205, 213 are secured indirectly to the elongated body 101 through an intermediate element, for example, a housing 215 for the local actuator 103. In some embodiments, the first SMA actuator 207 is coupled with the movable element 209 and the second element 213, and the biasing element 211 is coupled with the movable element 209 and the first element 213. In another embodiment, the local actuator 103 comprises only a first element 205, a movable element 209, and a single SMA actuator 207 coupled with the movable element 209 and the first element 205. The single SMA actuator 207 moves the movable element 209 in a first direction when actuated.

Figure 2C:
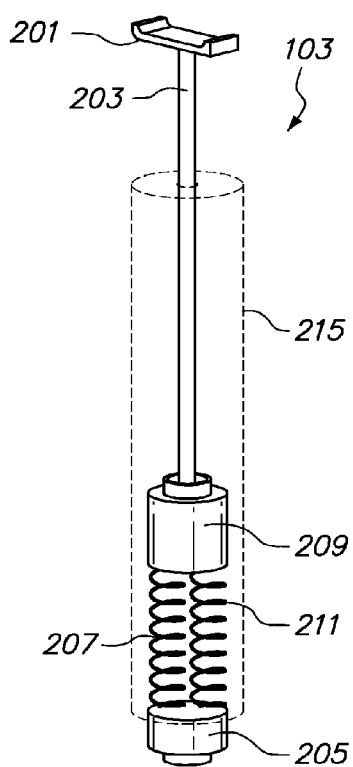
FIG. 2C is a partial cut-away side view showing an embodiment of a local actuator.
Figure 2D:
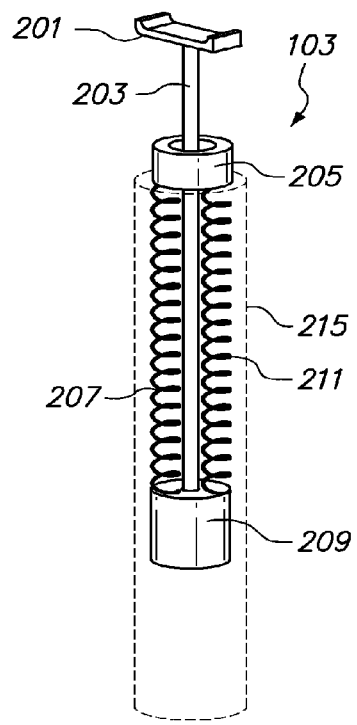
FIG. 2D is a partial cut-away side view showing an embodiment of a local actuator.
Figure 2E:
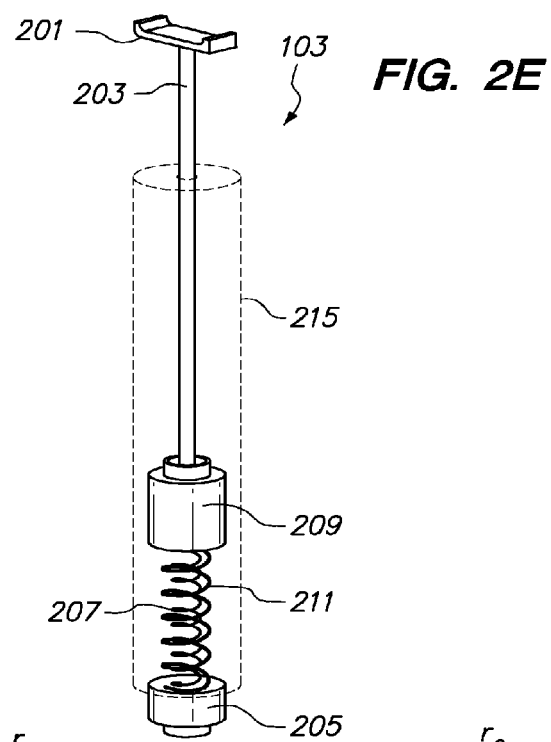
FIG. 2E is a partial cut-away side view showing an embodiment of a local actuator.

FIGS. 2C-2E show embodiments of a local actuator 103 where a first SMA actuator 207 and biasing element 211 are configured in parallel to one another. The first SMA actuator 207 is connected to a first element 205 that is secured to and preferably does not move relative to an elongated body 101.

The other end of the first SMA actuator 207 is coupled with a movable element 209. Similarly, a biasing element 211 is coupled with the first element 205 and the movable element 209. The biasing element 211 can comprise any deformable component, for example, a spring or second SMA actuator, and can be configured to apply a force on the movable element 209 that is counter to the force applied on the movable element by the SMA actuator 207 when the first SMA actuator 207 is activated. In FIG. 2C, the movable element 209 is disposed between the cam 201 and the first element 205. In FIG. 2D, the first element 205 is disposed between the movable element 209 and the cam 201. In FIG. 2E, the SMA actuator 207 and the biasing element 211 are disposed concentrically around the shaft 203. Thus, one of skill in the art will recognize that a first SMA actuator can optionally be paired with another biasing element 211 in parallel or series to produce a linear oscillating motion for a connected movable element 209.

As shown in the embodiments in FIGS. 2A-2E, the movable element 209 is connected to or comprises an arm or shaft 203 such that movement of the movable element 209 results in movement of the shaft 203. The shaft 203 can extend from the movable element 209 towards the distal end of the elongated body 101. In some embodiments, the shaft 203 can optionally extend from the movable element 209 towards the proximal end of the elongated body 101. The first element 205 and second element 213 optionally include openings to allow at least a portion of the shaft 203 to pass through the first and/or the second elements. One of skill in the art will recognize that the shaft 203 can be offset such that it does not have to pass through the first or second elements 205, 213 in order to extend through or move past these elements. For example, a portion of the shaft 203 can extend laterally from the movable element 209 and then turn and extend along an axis that is generally parallel to the longitudinal axis. In some embodiments, the shaft 203 itself can be used in place of a movable element 209 by directly connecting the SMA actuator 207 to the shaft 203. In other embodiments, the movable element 209 and shaft 203 are an integral component.

A distal end of the shaft 203 is coupled to or comprises a cam 201 that is configured to move along with the movable element 209 and the shaft 203 as the first SMA actuator 207 is alternated between an activated and a deactivated state. The cam 201 is configured to engage, for example, contact, pull, or push, another object. In some embodiments, the cam 201 is configured to engage an ultrasound transducer element in order to move the ultrasound transducer element between at least a primary position and a secondary position as the movable element 209 moves back and forth between two positions. In some embodiments, the cam 201 is configured to engage an ultrasound transducer element in order to rotate the ultrasound transducer element between at least a primary position and a secondary position as the movable element 209 linearly moves back and forth between a first position and a second position. In other embodiments the shaft 203 directly contacts an ultrasound transducer element. In some embodiments, the movable element 209, shaft 203, and cam 201 are a single movable piece. In other embodiments, the movable element 209, shaft 203, and cam 201 are each separate pieces connected to one another. In one embodiment, a simple pin joint is disposed between the shaft 203 and an ultrasound transducer element. The pin joint, or similar structure, is configured to convert linear motion into rotational motion.

The cam 201, shaft 203, and movable element 209 can be connected in various configurations. In some embodiments, the shaft 203 comprises more than one piece or member that move relative to one another. For example, in one embodiment, the shaft 203 comprises a first link that is pivotally connected to the movable element 209 and a second link that is pivotally connected to the first link and the cam 201. In some embodiments, the shaft 203 extends in a direction that is not substantially parallel to the longitudinal axis or has a portion that extends in a direction that is generally normal to the longitudinal axis. In some embodiments, the shaft 203 may be pivotally connected to the movable element 209 and/or the cam 201. In some embodiments, the shaft 203 moves relative to the movable element 209 and/or the cam 201. In some embodiments, the cam 201 may move, flex, or deflect, relative to the shaft 203 and/or movable element 209. In some embodiments, the cam 201 is pivotally connected to the shaft 203. In other embodiments, the cam 201 comprises a flexible material.

Figure 3A:
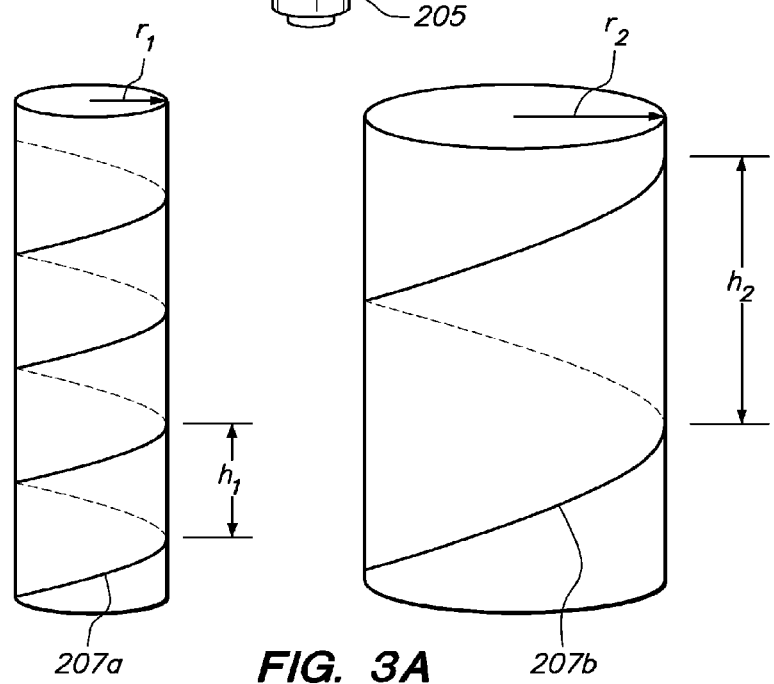
FIG. 3A is a diagram showing how the rotational motion of a SMA actuator is controlled.
Figure 3B:
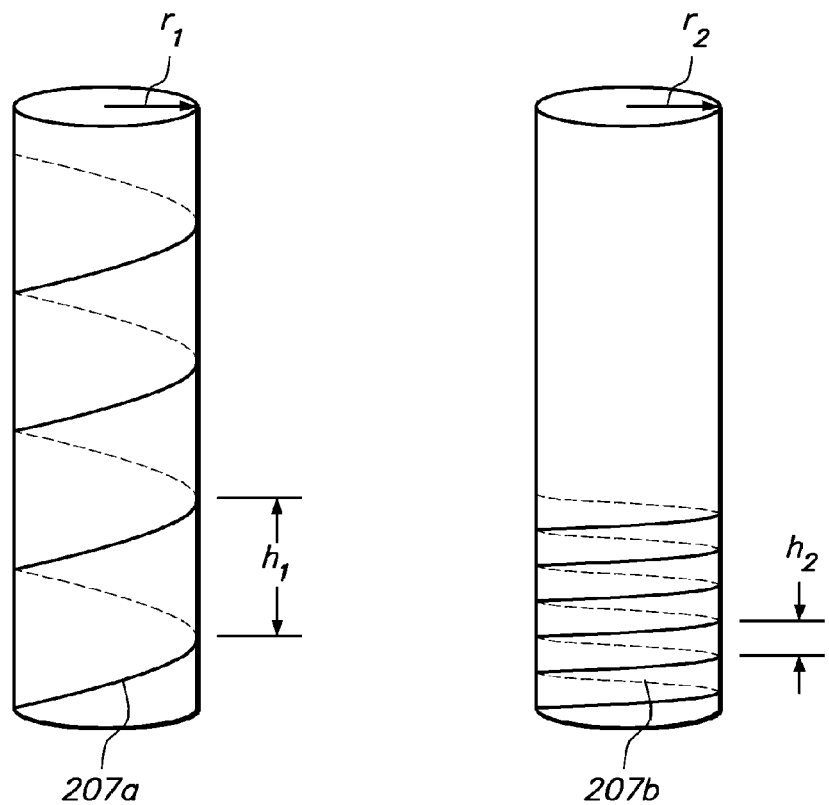
FIG. 3B is a diagram showing how the longitudinal motion of a SMA actuator is controlled.

FIGS. 3A and 3B are diagrams showing how the motion of a SMA actuator comprised of nitinol is controlled. For the sake of simplicity, FIG. 3A shows how the rotational motion of a SMA shaft is controlled and FIG. 3B shows how the longitudinal motion of a SMA shaft is controlled. However, one can combine the configurations illustrated in the two diagrams to achieve both rotational and longitudinal motion simultaneously.

FIG. 3A shows an SMA actuator 207 in a Martensite State and the same SMA actuator 207 in an Austenite State. The SMA actuator 207 is helically shaped. In the Martensite State, the SMA actuator 207 has a pitch (e.g., the height of one full turn) defined as hi, a radius defined as ri, and the length of the wire making one complete rotation is defined as Li. In the Austenite State, the SMA actuator 207 has a pitch defined as $h_2$ and a radius defined as $r_2$, and the length of the wire making one complete rotation is defined as Li. The relationship between the helix radius, pitch, and wire length is defined by the Pythagorean Theorem as:

$$(A_1 f + (2\pi r_x Y = (L_1)^2 \quad \text{[Equation 1]}$$

and $$(A_2 \ddot{Y} + (2\pi r_2 Y = (L_2)^2 \quad \text{[Equation 2]}.$$

Ignoring any contraction effects, the length of the wire wrapped into the helix remains the same regardless of the helical shape that it forms. To simplify, an assumption can be made that the wire makes one complete helical turn in the austenite state. Therefore, $$(A_1 f + (2\pi r_x Y = (L_1)^2 \quad \text{[Equation 3]}$$

and $$n = h_x) = h_2 \quad \text{[Equation 4]}$$

wherein n is the number of turns the helix makes around in the Martensite State. By substituting equations 3 and 4 into equations 1 and 2 and solving for n, we are left with the following relationship:

$$Yn = \quad \text{[Equation 5]}$$

This relationship indicates that the maximum achievable rotation is defined by the ratio of the radii in the Austenite State and the Martensite State. A partial transformation of the nitinol SMA actuator 207 from the lower temperature Martensite State to the high temperature Austenite State will result in a proportional reduction in achieved rotation. One can choose the desired level of rotation by selecting the appropriate ratio between the two radii.

FIG. 3B shows a SMA actuator 207 in a Martensite State and an Austenite State. In the Martensite State, the SMA actuator 207 has a pitch (e.g., the height of one full turn)

defined as hi and a radius defined as ri, the length of the wire making one complete rotation is defined as Li, and the number of helical turns is defined as nj. In the Austenite State, the SMA actuator 207 has a pitch defined as $h_2$ and a radius defined as $r_2$, the length of the wire making one complete rotation is defined as Li, and the number of helical turns is defined as $n_2$. The relationship between the helix radius, pitch, and wire length is defined by the Pythagorean Theorem disclosed in equations 1 and 2. The longitudinal motion of the SMA actuator 207 between the Martensite State and Austenite State can be determined by the following equation:

$$\text{Longitudinal motion} = (n_1 X h_1) - (n_2 X h_2) \quad \text{[Equation 6]}$$

Figure 4A:
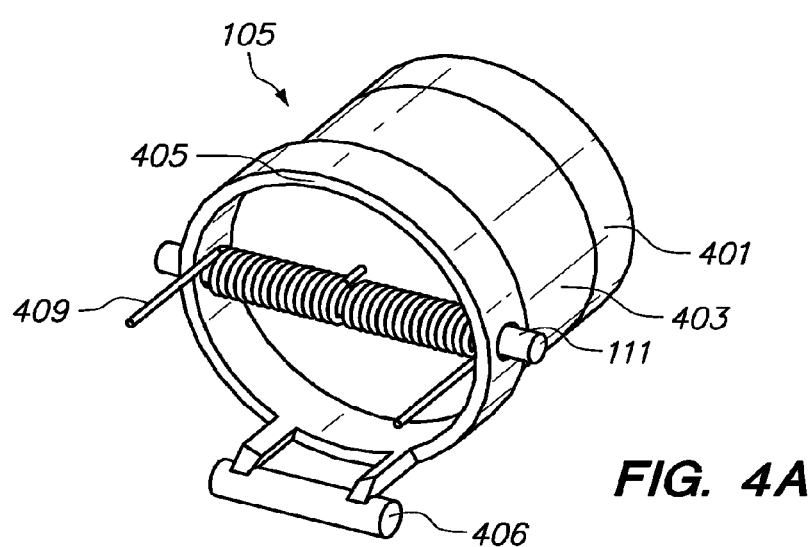
FIG. 4A is a perspective view of an embodiment of an ultrasound transducer element configured to rotate about a coupling member.

FIG. 4A shows an embodiment of an ultrasound transducer element 105 that includes a transducer 401, a transducer mount 405, a coupling member 111, and an electrical wire 409. The transducer 401 includes at least one ultrasound transducer crystal configured to send and receive ultrasound signals and the transducer 401 is preferably mounted on a backing 403. The transducer 401 can have various shapes, for example, square or cylindrical. In some embodiments, the transducer 401 is directly coupled with a transducer mount 405. The shape and size of the transducer mount 405 can vary depending on the shape and size of the transducer 401 or backing 403, to be coupled with the mount 405. In some embodiments, the transducer mount 405 is ring shaped with an aperture through the mount 405. In some embodiments, the transducer mount 405 includes a recess or indentation configured to receive at least a portion of a cam when the cam is engaged with the transducer mount.

The transducer mount 405 can optionally include a push bar 406 configured to engage a cam 201. The push bar 406 can be a pin, bar, cylinder, or similar structure that extends from the body of the transducer mount 405 to provide a point of contact for a cam 201. In some embodiments, the cam 201 engages one general side of the push bar 406 and in other embodiments, the cam 201 engages more than one side or portion of the push bar 406. In some embodiments, the cam 201 is fixed to the push bar 406 or transducer 405 and in other embodiments, the cam 201 is not fixed to the push bar 406.

In some embodiments, the transducer 401 can be made to have a thickness or length that is between about 5 μm and about 1500 μm, with a preferred size being between about 5 μm and about 1000 μm, or more preferably between about 200 μm and about 700 μm. The transducer 401 preferably has a thickness or length that is, is about, is at least, is at least about, is not more than, is not more than about 5, 10, 20, 30, 40, 50, 60, 70, 80, 90, 100, 200, 300, 400, 500, 600, 700, 800, 900, 1000, 1100, 1200, 1300, 1400 or 1500, μm or within a range defined by, and including, any two of these values.

In the illustrated embodiment, the transducer mount 405 has or is coupled with a coupling member 111 such that the transducer mount and transducer 401 are configured to rotate about the coupling member. In other embodiments, the transducer mount 405 and/or transducer 401 are directly coupled with an elongated body or other fixed object and configured to rotate about an axis of rotation relative to the elongated body or other fixed object. The coupling member 111 can have various shapes and sizes depending on the transducer mount 405 and/or the transducer 401. For example, the coupling member 111 can include a cylindrical pin, cylindrical dowel, or differently shaped member. In other embodiments, the transducer mount 405 and/or transducer 401 are configured to rotate about a different revolute joint, for example, a cylindrical joint, a screw joint, or a ball and socket joint. For example, a transducer mount 405 may include a ball and the elongated body 101 may include a socket configured to receive at least a portion of the ball to facilitate rotation of the transducer mount 405 relative to the elongated body 101. In another example, the transducer mount 405 may include one or more pins configured to rotate relative to one or more openings or sockets in the elongated body 101. Alternatively, the transducer mount 405 has a socket or opening for a ball or pin disposed on the elongated body 101. In some embodiments, the ultrasound transducer element 105 is configured to rotate around an axis of rotation that is substantially normal to the longitudinal axis. In some embodiments, the ultrasound transducer element 105 is configured to rotate around an axis of rotation that is not substantially normal to the longitudinal axis. In one embodiment, the axis of rotation of the ultrasound transducer element 105 may form about a 45 degree angle with the longitudinal axis.

In some embodiments, the electrical wire 409 is connected to the transducer 401. For example, in one embodiment, the electrical wire 409 is connected to the proximal surface of the transducer 401. In another embodiment, multiple electrical wires, for example, two, are connected to two or more surfaces of the transducer 401. The wire 409 can be the same as wire 109 in FIG. 1. The wire 409 can connect the transducer 401 with an electrical cable, for example, a coaxial or twisted pair, that is connected to an imaging system. In some embodiments, a wireless transmitter (not shown) is used to connect the transducer 401 to an imaging system. In some embodiments, the transducer mount 405 acts as an electrical conductor. In an embodiment, electrical wires 409 are coupled to the transducer 401 through non-contact coupling (e.g., capacitive or inductive coupling) which is commonly used in conventional intravascular imaging systems.

The electrical wire 109 can have various shapes and sizes. For example, the electrical wire 109 can have a generally circular cross-section with a diameter of about 100 μm. The electrical wire 109 preferably has a diameter that is, is about, is at least, is at least about, is not more than, is not more than about 1, 2, 3, 4, 5, 6, 7, 8, 9, 10, 20, 30, 40, 50, 60, 70, 80, 90, or 100 μm, or within a range defined by, and including, any two of these values.

In some embodiments, the electrical wire 409 is wrapped at least partially around the coupling member 111 or other portion of the transducer mount 405 such that it acts to bias the transducer 401 and transducer mount 405 in a certain direction. In one embodiment, the electrical wire 409 forms a coil around the coupling member 111 that acts as a mechanical spring that stores elastic energy as the transducer 401 rotates in a first direction and applies the energy to bias the transducer 401 in a direction counter to the first direction. Thus, the electrical wire 409 can be used to return the transducer mount 405 and transducer 401 to a primary position after the transducer mount and transducer 401 have rotated or moved away from the primary position to a secondary position. Utilizing the electrical wire 409 as a biasing force eliminates the need for additional force or resistance for the scanning motion resulting in a device 100 that is more efficient (e.g., requires less energy) and has a longer scanning time producing better imaging quality. In embodiments where an electrical wire 409 or other structure applies a biasing force on the transducer mount 405, the device 100 requires less energy to operate. One of skill in the art will understand that a spring or similar biasing structure that is not an electrical wire coiled around the coupling member 111 can also be used to bias the transducer mount 405 and transducer 401 towards a certain direction or position.

In a preferred embodiment, the ultrasound transducer element 105 rotates about an axis of rotation as another object, for example, a cam, applies a linear force on the transducer mount 405. In some embodiments, the ultrasound transducer element 105 continues to rotate after a force is applied on the transducer mount due to the moment of inertia of the transducer 401 and/or transducer mount 405. Generally, the higher moment of inertia is, the more the ultrasound transducer element 105 will continue to rotate after a linear force is applied to the transducer mount 405. The moment of inertia is mostly determined by the center of mass of the rotating body and the distance between the center of mass and the axis of rotation. Thus, the moment of inertia of the rotating portions of the ultrasound transducer element 105 can be adjusted by adjusting the mass, size, and location of the rotating portions. For example, a longer transducer element 401 is used to increase distance from the center of mass of the transducer element 401 and the axis of rotation.

The size of the ultrasound transducer element 105 itself contributes largely to the overall ultrasound device 100 size, so it is important that a smaller transducer 401 produces an image with quality that is comparable to a lager transducer 401. Increasing the density of any backing layer 403 or transducer mount 405 can minimize the transducer length and overall ultrasound transducer element 105 size.

Figure 4B:
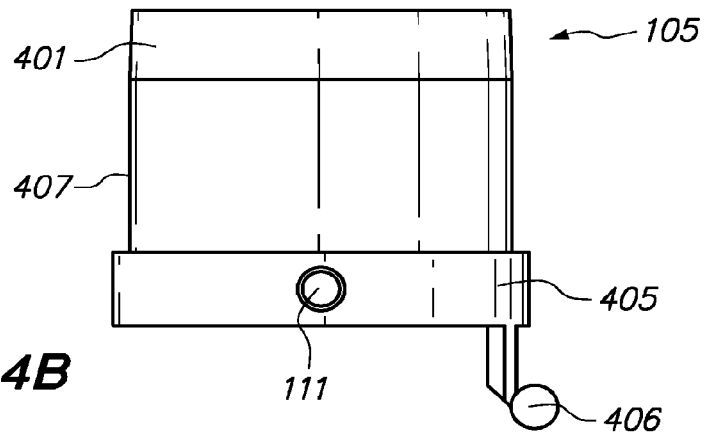
FIG. 4B is a side view of an embodiment of an ultrasound transducer element.
Figure 4C:
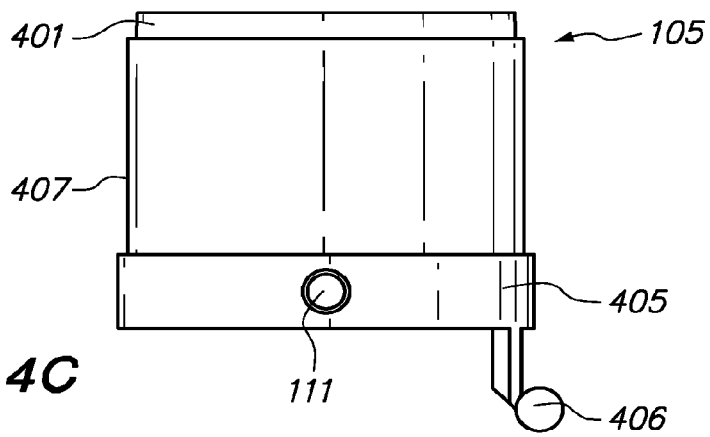
FIG. 4C is a side view of an embodiment of an ultrasound transducer element.

As shown in FIGS. 4A and 4B, in some embodiments, the moment of inertia of the rotating portions of the ultrasound transducer element 105 can be increased by adding a high density material layer 407, optionally the same as the backing 403. FIG. 4B shows an embodiment of an ultrasound transducer element 105 with a high density material layer 407 added between the transducer 401 and the transducer mount 405. The high density material layer 407 can comprise any high density material, for example, stainless steel, tungsten, gold, silver, platinum, copper, or titanium. FIG. 4C shows another embodiment with a tubular high density material layer 407 that is placed around the transducer 401 to add mass to the rotating elements of the ultrasound transducer element 105. In other embodiments, a combination of a high density backing layer 407 and tubular structure are used to increase the moment of inertia.

In some embodiments, the volume of the ultrasound transducer element 105 is about 0.1 cubic mm. In other embodiments, the volume of the ultrasound transducer element 105 is, is about, is at least, is at least about, is not more than, is not more than about 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, or 0.3 cubic mm. In some embodiments, the mass of the ultrasound transducer element 105 is about 1 mg. In other embodiments, the mass of the ultrasound transducer element 105 is, is about, is at least, is at least about, is not more than, is not more than about 0.2, 0.3, 0.4, 0.5, 0.6, 0.7, 0.8, 0.9, 1, 1.1, 1.2, 1.3, 1.4, 1.5, 1.6, 1.7, 1.8, 1.9, 1.8, or 2 mg, or within a range defined by, and including, any two of these values. In some embodiments, the ultrasound transducer element 105 may be generally cylindrical with a diameter or width that is, is about, is at least, is at least about, is not more than, is not more than about 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or 3 mm, or within a range defined by, and including, any two of these values. In some embodiments, the ultrasound transducer element 105 has a height that is, is about, is at least, is at least about, is not more than, is not more than about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, or 2.5 mm, or within a range defined by, and including, any two of these values.

Figure 5:
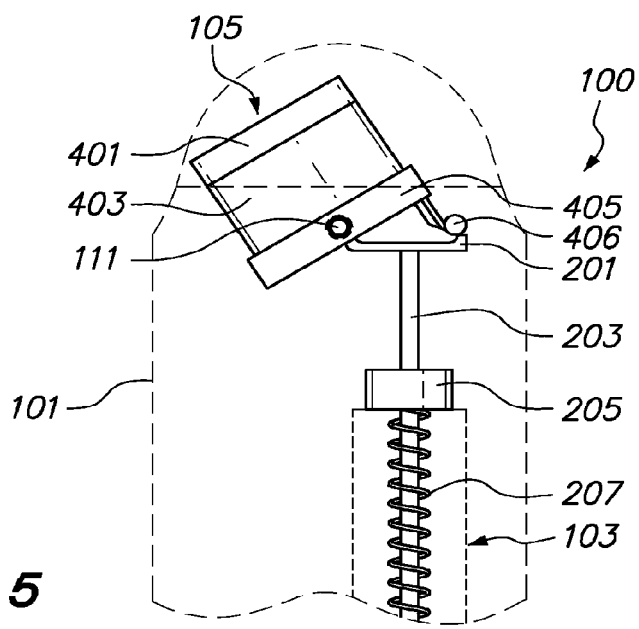
FIG. 5 is a partial cut-away side view of an embodiment of a forward-looking ultrasound imaging device.
Figure 7B:
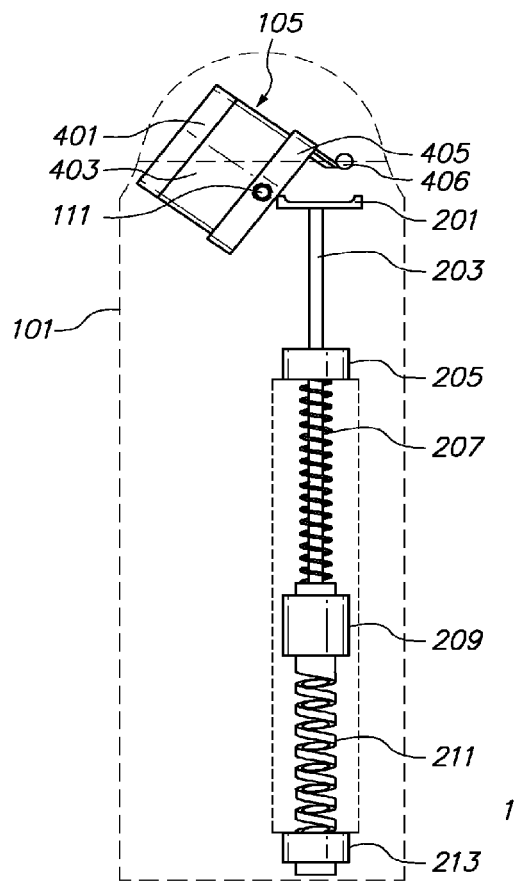
FIG. 7B is a partial cut-away side view of the forward-looking ultrasound imaging device shown in FIG. 7A showing the ultrasound transducer element in a different position.
Figure 7C:
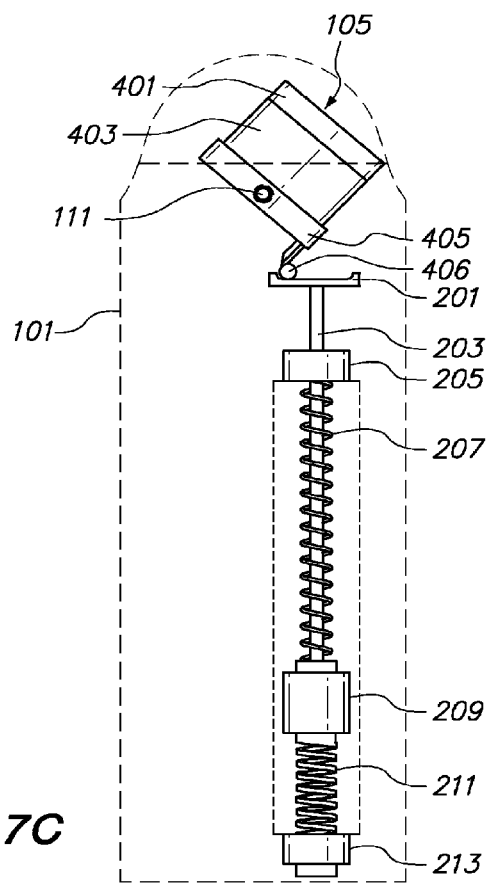
FIG. 7C is a partial cut-away side view of the forward-looking ultrasound imaging device shown in FIG. 7B showing the ultrasound transducer element in a different position.
Figure 7D:
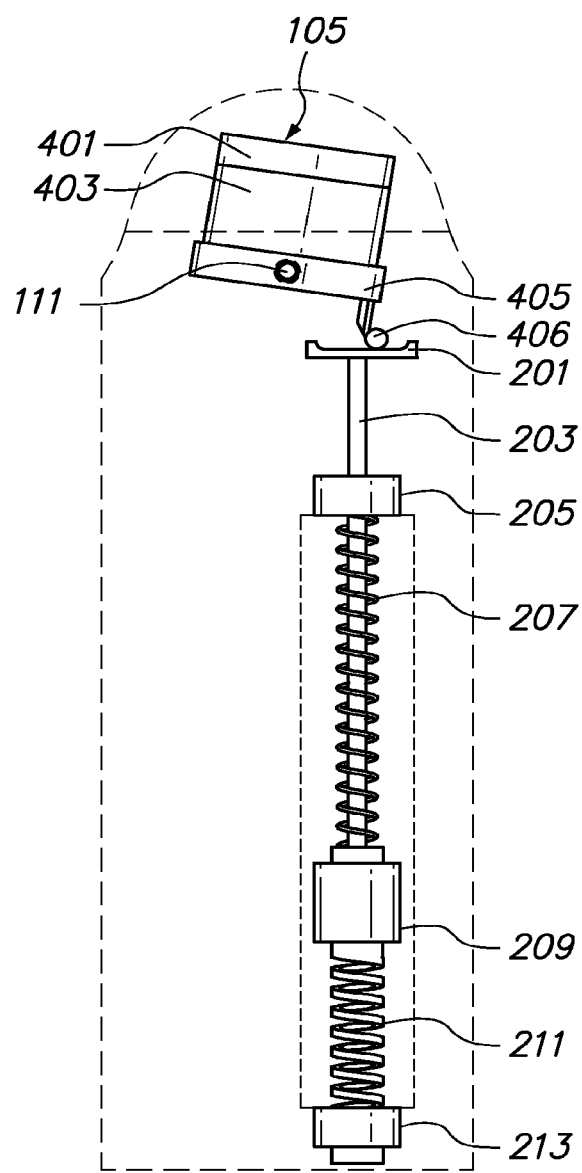
FIG. 7D is a partial cut-away side view χ>f the forward-looking ultrasound imaging device shown in FIG. 7C showing the ultrasound transducer element in a different position.

FIG. 5 shows an embodiment of an intravascular ultrasound device 100 including a local actuator 103 and an ultrasound transducer element 105 configured to rotate about an axis of rotation and a coupling member 111 relative to the elongated body 101. The cam 201 of the local actuator 103 is configured to move in a first linear direction and a second linear direction that is counter to the first linear direction along with the movable element 209 (not shown). In some embodiments, when moving in a linear direction, the cam 201 engages the transducer mount 405 at the push bar 406 and causes the ultrasound transducer element 105 to rotate about the axis of rotation in a first direction.

In general, the first SMA actuator 207 is used to generate a large linear displacement which has intrinsic limitations on how fast it moves and how much power it requires. In some embodiments, because of geometric constraints (e.g., the dimensions of a vasculature) the cam 201 can collide with the transducer mount 405 other than at the push bar 406 when moving in first a linear direction causing the cam 201 to stop moving in the first linear direction and causing the ultrasound transducer element 105 to stop rotating before the desired amount of rotation of the transducer element 105 is achieved. For example, if the cam 201 is configured to push the transducer mount 405 to cause the ultrasound transducer element 105 to rotate, it works fine within a certain angle of rotation (e.g., less than about 60°) but is limited when pushing farther to cause a larger angle of rotation (e.g., up to about 180°). In some embodiments, when the cam 201 pushes on the push bar 406 for longer distances, the cam 201 starts colliding with the transducer mount 405 and the rotation of the ultrasound transducer element 105 is stopped prematurely.

The problem of the cam 201 colliding with the transducer mount 405 where not desired can be addressed by configuring the local actuator 103 to apply an amplified force or impulse force to the ultrasound transducer element 105. Applying an impulse force to the ultrasound transducer element 105 utilizes the moment of inertia of the ultrasound transducer element 105 to rotate the ultrasound transducer element 105 about the axis of rotation after the cam 201 and the push bar 406 portion of the transducer mount have disengaged from one another. In one embodiment, the cam 201 pushes the ultrasound transducer element 105 to a certain point and the transducer element 105 continues to rotate beyond where the cam 201 stops because of the moment of inertia. In embodiments where the ultrasound transducer element 105 includes an electrical wire 109, or other elastic element, configured to bias the ultrasound transducer element 105 in a certain direction counter to the direction of rotation caused by the impulse force, the ultrasound transducer element 105 will return back to a primary position or origin due to the applied biasing force. In some embodiments, the biasing element 211 in the local actuator 103 is optionally omitted and the electrical wire 409, or other biasing element in the transducer element 105, returns the cam 201 and movable element 209 to the starting position as ultrasound transducer element 105 rotates to its starting or primary position.

Turning now to FIGS. 6A-6C, an embodiment of an intravascular ultrasound device 100 including a local actuator 103 configured to apply an upward force on the transducer mount 405 is shown. FIG. 6A shows the cam 201 and the transducer mount 405 initially engaged in a primary position. The first SMA actuator 207 is activated to move the movable element 209 towards the distal end of the elongated body 101. The shaft 203 and cam 201 move along with the movable element 209 and engage the transducer mount 405 and push bar 406. The transducer mount 405 begins to rotate counter-clockwise while the cam 201 continues to move towards the distal end. In another embodiment, if the moment of inertia of the transducer element 105 is high enough, the shaft 203 can directly push the transducer mount 405, or the ultrasound transducer element 105, and a cam 201 is not necessary to achieve the leverage in the scanning motion.

FIG. 6B shows an example of a point where the movable element 209, shaft 203, and cam 201 stop moving towards the distal end and the cam 201 and transducer mount 405 disengage from one another. At this point, the first SMA actuator 207 is preferably deactivated and the biasing element 211 causes the movable element 209, shaft 203, and cam 201 to move in the opposite direction (e.g., towards the position in FIG. 6A). Even though the cam 201 and transducer mount 405 disengage at this point, the ultrasound transducer element 105 preferably continues to rotate counter-clockwise about the axis of rotation and coupling member 111. The ultrasound transducer element 105 may continue to rotate about the axis of rotation after disengagement from the cam 201 because of the moment of inertia of the ultrasound transducer element 105. The transducer element 105 may also include an optional biasing element that assists the continued rotation of the transducer element 105 in the counter-clockwise direction after the transducer mount 405 disengages from the cam 201. For example, the ultrasound transducer element 105 may include a spring configured to bias the transducer element to rotate counter-clockwise about the axis of rotation of the coupling member 111.

As shown in FIG. 6C, the ultrasound transducer element 105 can continue to rotate counter-clockwise to a secondary position where the electrical wire 109 or similar structure biases the ultrasound transducer element 105 to rotate in a counter direction (e.g., clockwise) back towards its origin or primary position. The biasing element 211 will move the movable element 209, shaft 203, and cam 201 back to their initial or primary position (e.g., the position in FIG. 6A) and the ultrasound transducer element 105 can continue rotating until it contacts the cam 201 in the first position or until it reaches some other equilibrium. Thus, the oscillating linear movement of the movable element 209, shaft 203, and cam 201 can be used to rotate the ultrasound transducer element 105 back and forth about an axis of rotation to create a forward-looking sweeping motion of the transducer 401. In another embodiment, one or more mechanical stops (not shown) are included to further limit the rotation of the ultrasound transducer 105.

The device 100 can be configured for side-looking as well as forward-looking, for example, by placing an ultrasound transducer element 105 or a reflective surface (not shown) such as a mirror in different configurations. In some embodiments, the angle of orientation of the ultrasound transducer element 105 or mirror relative to the longitudinal axis of the device 100 is any angle between about 15° and about 165°, with the preferred angle for side-looking device 100 being between about 80° and about 110°. Angles contemplated include about 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, and about 165 degrees, or within a range defined by, and including, any two of these values.

The range of motion generated by the local actuator 103 described herein will vary depending of the application. Rotational motion of the transducer element can oscillate in a range from about 1 or 2 degrees up to about 270 degrees. The angle of rotational displacement that can be generated by the local actuator 103 is, is about, is at least, is at least about, is no more than, or is no more than about, 1, 2, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 190, 200, 210, 220, 230, 240, 250, 260, or 270 degrees, or within a range defined by, and including, any two of these values. In a preferred embodiment the transducer 401 scans an equivalent direction to either side of the longitudinal axis, such that the device 100 is imaging directly in front of the distal tip of the device. Also it is possible to amplify the angular displacement by simply utilizing different shapes of the transducer mount 405, especially where it has an interaction/contact with the cam 201. In other embodiments, the scanning motion is directed to one side of the device, such that the imaging field is not symmetrical relative to the longitudinal axis. By adjusting the speed of scanning motion, the scanning rate can be adjusted while the device is in the patient, allowing the operator to adjustably define a specific frame rate in real-time images. The preferred range of rotational displacement or angle of rotation generated by the device 103 is from about 30 to 180 degrees. In addition, it is possible to use the device 100 for single point interrogation for optical coherence reflectometry or Doppler Effect measurements.

FIGS. 7A-7D show another embodiment of an intravascular ultrasound device 100 where the first SMA actuator 207 is configured to expand and push the movable element 109 down (e.g., away from the distal end of the elongated body 101) and the biasing element 211 is configured to move the movable element 209 and cam 201 towards the distal end. When the first SMA actuator 207 pushes the movable element 109 down, the shaft 203 moves with the movable element and pulls the cam 201 down as well. As the cam 201 moves down, the electrical wire 109 or other biasing force causes the ultrasound transducer element 105 to rotate clockwise, following the cam. In some embodiments the cam 201 and the transducer mount 405 can maintain engagement as the cam 201 moves down. In other embodiments, the cam 201 and movable element 209 move faster than the ultrasound transducer element 105 resulting in disengagement between the cam 201 and the transducer mount 405. The biasing element 211 is configured to move the movable element 209 and cam 201 back up to the first position shown in FIG. 7A. As the biasing element 211 causes the cam 201 to move towards the distal end to its starting position, the cam 201 and transducer mount 405 is engaged, or re-engage, causing the ultrasound transducer element 105 to rotate counter-clockwise and return to its primary or starting position (e.g., the position shown in 7A). In another embodiment, the cam 201 is configured to pull the transducer mount 405 down, optionally releasing the transducer mount 405 at a certain point. The electrical wire 409 or biasing force then causes the ultrasound transducer element 105 to rotate in a counter direction back to its primary position or origin.

FIGS. 8A and 8B show an embodiment where the cam 201 pulls instead of pushing the push bar 406. FIG. 8A shows the cam 201 and push bar 406 initially engaged in a primary position. The first SMA actuator 207 is activated to move the movable element 209 away from the distal end of the elongated body 101 pulling the push bar 406 and causing the ultrasound transducer element 105 to rotate clockwise towards a secondary position.

FIG. 8B shows the ultrasound transducer element 105 in the secondary position. The ultrasound transducer element 105 can include a biasing element, for example, a coiled electrical wire 409 or spring (not shown), configured to bias the ultrasound transducer element 105 towards the primary position. In some embodiments, the linear actuator 103 does not require a biasing element or second SMA actuator 211 to return the cam 201 to the primary position because the biasing element in the ultrasound transducer element 105 pulls the cam 201 back to the primary position when the first SMA actuator 207 is deactivated. In some embodiments, the local actuator 103 includes a biasing element 211 such that the cam 201 pushes and pulls the transducer mount 405 in opposite directions resulting in a sweeping rotation movement of the ultrasound transducer 105.

It is desirable to provide quality imaging for a physician to interpret accurately during an intervention. There are different ways to improve and achieve higher quality imaging. One way is to have a smooth and consistent scanning motion. Another way is to acquire as much data as possible and process the data through averaging and filtering in order to enhance different characteristics, for example, the signal to noise ratio. Thus, image quality can be enhanced by providing a consistent scanning motion and adjusting the time the scanning motion takes. To achieve an ideal scanning motion, an actuator drive waveform can be optimized to produce a consistent motion while maximizing the scanning time to acquire as much data as possible.

Figure 9A:
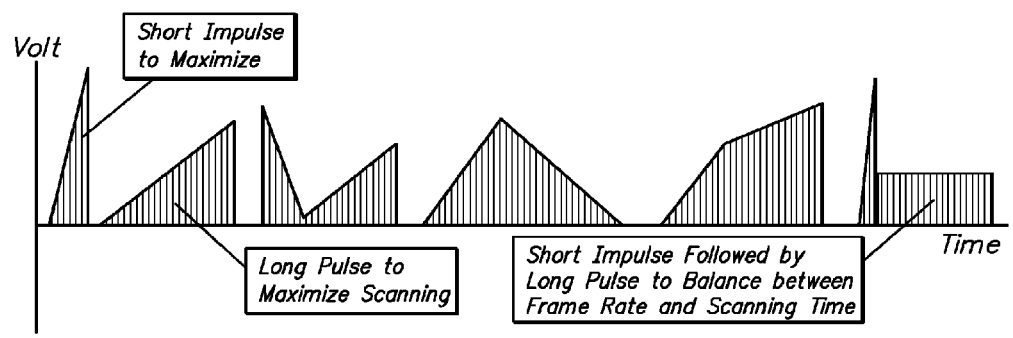
FIG. 9A is a diagram showing waveforms of voltage versus time that is used to produce different scanning motions for a transducer element in a forward-looking imaging device.
Figure 9B:
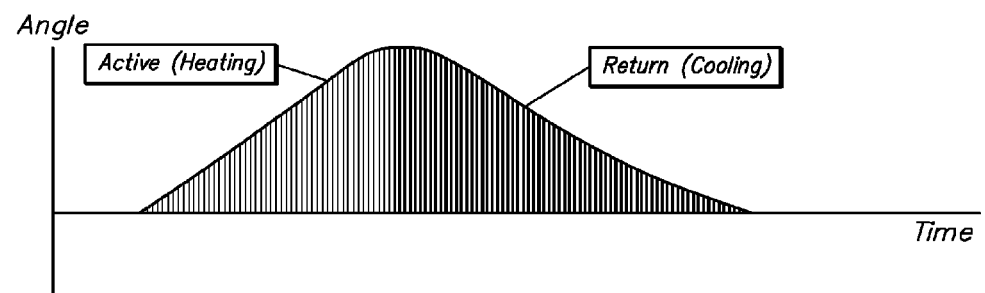
FIG. 9B is a diagram showing the angle of rotation versus time for a transducer element in a forward-looking imaging device during an active path and returning path.

FIG. 9A shows different examples of contemplated waveforms that can lead to different scanning motions. The wave forms are expressed as voltage versus time. FIG. 9B shows how an active heating path and cooling path affect rotation of an ultrasound transducer element. FIG. 9B shows the angle of rotation versus time for an active (heating) path and returning (cooling path).

The ultrasound device 100 must be able to operate for a certain period of time when used in invasive procedures. Depending on the type of intervention, the procedure could take a couple of hours or more and the ultrasound device 100 could be required to undergo about one million or more cycles of scanning. In general, SMA actuators are considered to have low fatigue properties and so it is critical, yet challenging, to achieve the required life cycle with a frame rate of 10 Hz or higher as an imaging device. SMA actuators are able to continuously operate in millions of cycles so long as they do not undergo a large displacement or strain. The main challenge to achieving a large scanning motion required for clinically vital imaging is to balance the displacement of the SMA actuator with the fatigue properties of the SMA. For example, typically, a large scanning motion requires a large displacement of an SMA actuator resulting in diminished longevity of the SMA due to fatigue failure. However, the motion amplification disclosed in a preferred embodiment herein makes it feasible and practical to meet both the displacement and fatigue requirements simultaneously. In some embodiments, because of the motion amplification, the SMA actuator 207 only needs to produce a small displacement and therefore, undergoes less strain while the ultrasound transducer element 105 undergoes a large scanning motion. Thus, embodiments disclosed herein can be used for relatively long periods of time while still meeting the requirements of functional imaging devices used in invasive medical procedures.

In some embodiments of an ultrasound device 100, it is desirable to provide real time imaging without losing valuable information during intervention. For real time imaging, certain frame rates are preferred depending on where to image. For example, for heart imaging, it is preferable to image a moving heart in a frame rate of 20 Hz or higher considering how fast it is moving. Conventionally it becomes challenging to drive the first SMA actuator 207 higher than 10 Hz because it requires enough cooling time to provide a practically functional motion. However, by utilizing the leverage present in preferred embodiments disclosed herein, it is possible to achieve a higher frame rate for imaging because the scanning motion is not largely determined by the first SMA actuator 207 itself. Also, to be able to drive the first SMA actuator 207 10 Hz or higher, the first SMA actuator 207 is typically in contact with water or other liquid that provides fast cooling. But embodiments disclosed herein make it possible to drive the first SMA actuator 207 at a frequency that is, is about, is at least, is at least about, is not more than, is not more than about 10 Hz, 15 Hz, 20 Hz, 25 Hz, 30 Hz or within a range defined by, and including, any two of these values. This makes the manufacturing process for the device simpler and easier as a commercial product because there is no need to seal or fill a device with water or other liquid during assembly and packaging. By driving the first SMA actuator 207 in air, it requires less energy and demands less power from an imaging system.

The first SMA actuator 207 is preferably surrounded by air. Air is a good insulator by itself, so it contributes to a lower operating temperature for the device 100 (e.g. the external temperature of the device while operating is, is about, is at least, is at least about, is not more than, is not more than about 25, 30, 35, 40, 43, 45, 50, 55, 60, 65, 70 degrees Celsius or within a range defined by, and including, any two of these values) which is more favorable considering possible negative effects on tissue when operating at high temperatures. In some embodiments, an optional housing 215 surrounding the first SMA actuator 207 (e.g. shown in FIG. 2A) is made of an insulating material that further heat insulates the first SMA actuator 207 from the rest of the device 100. Also, air makes the first SMA actuator 207 less susceptible to the surrounding environment, so it can produce consistent scanning motion regardless of blood flow, tissue, and body temperature.

The local actuator 103 can generate rotational displacement in a range from about 1Hz to about 50 Hz. The preferred frequency of motion is between about 8 Hz and 30 Hz. The frequency of movement generated by the local actuator 103 is, is about, is at least, is at least about, is not more than, is not more than about 1, 2, 3, 4, 5, 6, 7, 8, 9, 10, 11, 12, 13, 14, 15, 16, 17, 18, 19, 20, 25, 30, 35, 40, 45, or 50 Hz, or within a range defined by, and including, any two of these values.

The first SMA actuator 207 can preferably be activated at various speeds, depending on the frame rate. Preferably, the first SMA actuator 207 is activated at between O.lmSec and 50 mSec. It is contemplated that the first SMA actuator 207 is preferably activated at a time constant that is, is about, is at least, is at least about, is not more than, is not more than about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mSec, or within a range defined by, and including, any two of these values.

Figure 10A:
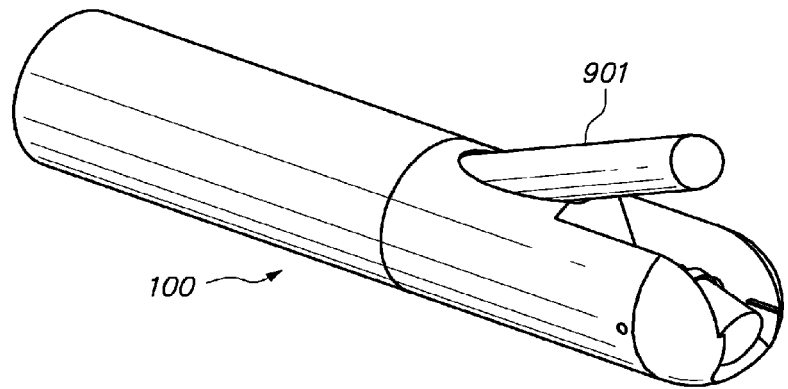
FIG. 10A is a perspective view of an embodiment of a forward-looking ultrasound imaging device.
Figure 10B:
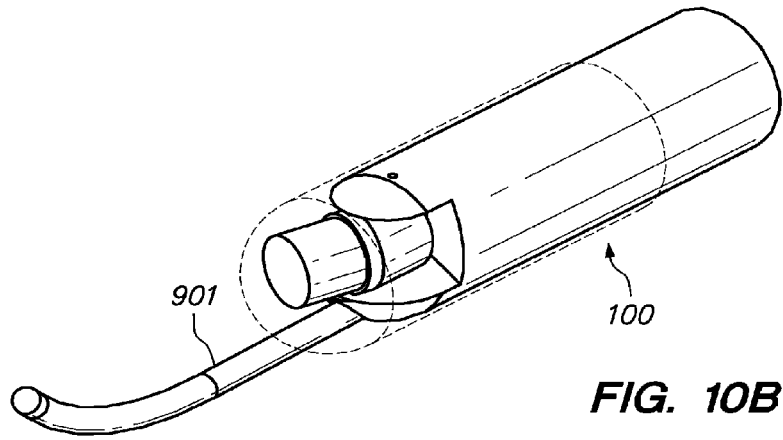
FIG. 10B is a partial cut-away perspective view of an embodiment of a forward-looking ultrasound imaging device.
Figure 10C:
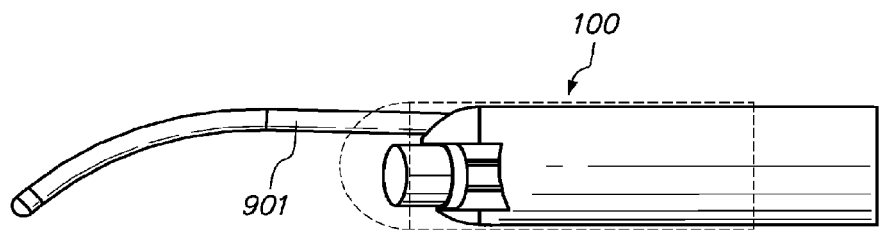
FIG. 10C is a partial cut-away side view of an embodiment of a forward-looking ultrasound imaging device.

As shown in FIGS. 10A-10C, the intravascular ultrasound device 100 disclosed herein can be implemented in various medical devices 901, for example, but not limited to, devices for stent placement and deployment, balloon angioplasty, directional atherectomy, cardiac ablation, PFO (patent foramen ovule) closure, transvascular re-entry, trans-septal punch, and CTO (chronic total occlusion) crossing. In another embodiment, the intravascular ultrasound device 100 can have a lumen or opening along the longitudinal axis configured to introduce a guide wire or other interventional devices, and provide real-time or nearly real-time guidance in front of or around the device. Another embodiment of the invention is a method of visualizing the interior of an organ or tissue having a lumen or cavity using the device described above.

For real-time imaging guidance, it is desirable to have a localized steering in the distal end of the device 100. In a preferred embodiment a localized steering portion can be incorporated near or around the distal imaging tip for efficient navigation. The local steering can be activated by one, two, three, four or more local actuators placed in the distal end, so it can be remotely controlled. Or the local steering can be achieved by simple pull wires (one, two, three, four or more) attached to or around the distal end that extends to the proximal end of the device, so it can be manually activated by hands. Depending on the number of local actuators and pull wires, it can have various motions with multiple degrees of freedom (one, two, three, four or more).

In some embodiments, the device 100 can provide intravascular ultrasound imaging in a small device such that it is easier to use in invasive procedures. Some medical devices incorporating the device 100 can have an outside diameter that is placed inside a patient's vasculature that is between about 2Fr and about 3.5Fr (about 0.6 mm to about 1.2 mm), although sizes as small as 1Fr (0.33 mm) are also contemplated. For peripheral applications, the outside diameter of the portion of the medical device placed in the patient's vasculature can be as large as about 12Fr (4 mm). Generally, it is contemplated that the outside diameter of any portion of the disclosed devices 100, including the proximal and/or distal ends, the main body of the device, or the portion of the device designed to be placed inside the patient, is, is about, is not less than, is not less than about, is not more than, is not more than about 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0 mm, or within a range defined by, and including, any two of these values.

In another embodiment, the intravascular ultrasound device 100 is combined with Fractional Flow Reserve (FFR), so a single device has the capability of the ultrasound imaging and FFR. FFR is able to measure the intravascular blood pressure which helps in determining the severity of intravascular stenosis. By combining two methods in a guide wire, a single guide wire can provide more useful information to guide complex interventional procedures. In some embodiments, the same transducer 401 can be used to do ultrasound imaging as well as pressure measurement. In other embodiments, a separate sensor can be embedded to measure the intravascular pressure.

The embodiments described above are largely directed to ultrasound imaging. However, devices incorporating the scanning mechanism are not limited to cardiovascular applications, and it is contemplated that the device can be used in other settings, preferably medical procedures, where visualization of a small lumen or cavity is required.

Although the embodiments described herein have the imaging devices and scanning mechanism located in the distal end of the apparatus or other elongate member, one of skill in the art will recognize that the imaging devices can be placed anywhere along the length of the device. In another embodiment, the imaging devices disclosed herein are integrated into the distal end of an device's rigid section that defines the distal tip of an apparatus.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A method, comprising:
providing an elongate body having a longitudinal axis, a proximal end portion, and a distal end portion;
coupling a local actuator to the elongate body adjacent the distal end portion, the local actuator including:
a first element that is fixedly secured to the elongate body when coupling the local actuator to the elongate body;
a first shape memory alloy (SMA) actuator coupled to the first element, wherein the first SMA actuator is configured to switch between an activated state and a deactivated state; and
a movable element coupled to the first SMA actuator, wherein the movable element is configured to move longitudinally substantially parallel to the longitudinal axis of the elongate body between a first position and a second position in response to the first SMA actuator switching between the activated and deactivated states; and
coupling an ultrasound transducer element to the elongate body adjacent to the local actuator such that the ultrasound transducer is configured to rotate between a primary position and a secondary position about an axis of rotation that is normal to the longitudinal axis of the elongate body; and
wherein the movable element is configured to intermittently engage the ultrasound transducer element when moving between the first position and the second position so as to cause the ultrasound transducer element to rotate about the axis of rotation.

2. The method of claim 1, wherein the local actuator further includes a biasing element coupled to the movable element and the first element, wherein the biasing element is configured to move the movable element from the second position to the first position.

3. The method of claim 1, wherein the local actuator further includes:
a second element that is fixedly secured to the elongate body when coupling the local actuator to the elongate body; and
a biasing element coupled to the second element and the movable element, wherein the biasing element is configured to move the movable element from the second position to the first position.

4. The method of claim 3, wherein the first and second elements are fixedly secured to the elongate body at positions spaced along an axis that is parallel to the longitudinal axis.

5. The method of claim 3, wherein the first and second elements are fixedly secured to the elongate body at positions spaced along an axis that is normal to the longitudinal axis.

6. The method of claim 3, wherein the biasing element of the local actuator comprises a second SMA actuator.

7. The method of claim 3, wherein the movable element is disposed between the first element and the second element.

8. The method of claim 1, further comprising electrically coupling an electrical wire to the ultrasound transducer element.

9. The method of claim 8, wherein the electrical wire biases the ultrasound transducer element towards the primary position when coupled to the ultrasound transducer element.

10. The method of claim 1, wherein the angle of rotation the ultrasound transducer element rotates about the axis of rotation between the primary position and the secondary position is between 5° and 185°.

11. A method, comprising:
    providing an elongate body having a longitudinal axis, a proximal end portion, and a distal end portion;
    coupling an actuator to the distal end portion of the elongate body, wherein coupling the actuator to the distal end portion includes:
        fixedly coupling a first element to the elongate body;
        fixedly coupling a second element to the elongate body at a position spaced from the first element;
        wherein a first shape memory alloy (SMA) actuator is coupled to the first element, wherein the first SMA actuator is configured to switch between an activated state and a deactivated state;
        wherein a movable element is coupled to the first SMA actuator, the movable element configured to move longitudinally between a first position and a second position in response to the first SMA actuator switching between the activated and deactivated states;
    pivotally coupling an ultrasound transducer element to the elongate body adjacent to the actuator such that the ultrasound transducer is configured to rotate between a primary position and a secondary position about an axis of rotation that is normal to the longitudinal axis of the elongate body as a result of intermittent engagement with the movable element as the movable element moves between the first and second positions.

12. The method of claim 11, wherein the actuator further includes a biasing element coupled to the movable element and the first element, wherein the biasing element is configured to move the movable element from the second position to the first position.

13. The method of claim 12, wherein the biasing element of the local actuator comprises a second SMA actuator.

14. The method of claim 11, wherein the second element is fixedly coupled to the elongate body at a position spaced from the first element spaced along an axis that is parallel to the longitudinal axis.

15. The method of claim 11, wherein the second element is fixedly coupled to the elongate body at a position spaced from the first element spaced along an axis that is normal to the longitudinal axis.

16. The method of claim 11, wherein the movable element is disposed between the first element and the second element.

17. The method of claim 11, further comprising electrically coupling an electrical wire to the ultrasound transducer element.

18. The method of claim 17, wherein the electrical wire biases the ultrasound transducer element towards the primary position when coupled to the ultrasound transducer element.

19. The method of claim 11, wherein the angle of rotation the ultrasound transducer element rotates about the axis of rotation between the primary position and the secondary position is between 5° and 185°.

20. The method of claim 19, wherein the ultrasound transducer element is positioned at a distal tip of the elongate body.

* * * * *